(12) United States Patent
Fallis et al.

(10) Patent No.: US 7,655,809 B2
(45) Date of Patent: Feb. 2, 2010

(54) COMPOUNDS COMPRISING A LINEAR SERIES OF FIVE FUSED CARBON RINGS, AND PREPARATION THEREOF

(75) Inventors: Alexander Graham Fallis, Ottawa (CA); Matthew Allen Heuft, Peterborough (CA); Christophe Bénard, Verrieres le Buisson (FR)

(73) Assignee: University of Ottawa, Ottawa, Ontario (CA)

( * ) Notice: Subject to any disclaimer, the term of this patent is extended or adjusted under 35 U.S.C. 154(b) by 638 days.

(21) Appl. No.: 11/130,190

(22) Filed: May 17, 2005

(65) Prior Publication Data

US 2005/0274945 A1    Dec. 15, 2005

Related U.S. Application Data

(60) Provisional application No. 60/571,940, filed on May 18, 2004.

(51) Int. Cl.
C09B 3/50 (2006.01)
H01L 51/10 (2006.01)

(52) U.S. Cl. .......................................... 552/284; 257/40
(58) Field of Classification Search .................. 257/40; 552/284
See application file for complete search history.

(56) References Cited

U.S. PATENT DOCUMENTS

| | | | | |
|---|---|---|---|---|
| 3,839,034 | A | 10/1974 | Wiedemann | 96/1.5 |
| 3,871,882 | A | 3/1975 | Wiedemann | 96/1.5 |
| 3,895,944 | A | 7/1975 | Wiedemann et al. | 96/1.5 |
| 3,977,870 | A | 8/1976 | Rochlitz | 96/1.5 |
| 3,989,520 | A | 11/1976 | Rochlitz | 96/1.5 |
| 4,072,520 | A | 2/1978 | Rochlitz et al. | 96/1.5 |
| 4,231,799 | A | 11/1980 | Rochlitz et al. | 430/59 |
| 5,141,671 | A | 8/1992 | Bryan et al. | 252/301.16 |
| 5,151,478 | A | 9/1992 | Chiang et al. | 526/258 |
| 5,151,629 | A | 9/1992 | VanSlyke | 313/504 |
| 5,707,779 | A | 1/1998 | Naito | 430/270.1 |
| 6,207,472 | B1 | 3/2001 | Callegari et al. | 438/99 |
| 6,284,562 | B1 | 9/2001 | Batlogg et al. | 438/99 |
| 6,344,284 | B1 | 2/2002 | Chou | 428/690 |
| 6,433,359 | B1 | 8/2002 | Kelley et al. | 257/40 |
| 6,452,207 | B1 | 9/2002 | Bao | 257/40 |
| 6,465,116 | B1 | 10/2002 | Ishikawa et al. | 428/690 |
| 6,500,604 | B1 | 12/2002 | Dimitrakopoulos et al. | 430/322 |
| 6,617,609 | B2 | 9/2003 | Kelley et al. | 257/40 |
| 6,690,029 | B1 | 2/2004 | Anthony et al. | 257/40 |
| 6,864,396 | B2 | 3/2005 | Smith et al. | 568/633 |
| 2001/0015438 | A1 | 8/2001 | Callegari et al. | 257/40 |
| 2002/0022150 | A1 | 2/2002 | Toguchi et al. | 428/690 |
| 2003/0097010 | A1 | 5/2003 | Vogel et al. | 552/208 |
| 2003/0100779 | A1 | 5/2003 | Vogel et al. | 552/271 |
| 2003/0116755 | A1 | 6/2003 | Takahashi | 252/500 |
| 2003/0136964 | A1 | 7/2003 | Afzali-Ardakani et al. | 257/72 |
| 2003/0144562 | A1 | 7/2003 | Afzali-Ardakani et al. | 570/212 |
| 2003/0213952 | A1 | 11/2003 | Iechi et al. | 257/40 |
| 2006/0267004 | A1* | 11/2006 | Fallis et al. | 257/40 |

FOREIGN PATENT DOCUMENTS

| | | |
|---|---|---|
| CA | 2213240 | 8/1996 |
| CA | 2344084 | 10/2002 |
| CA | 2253654 | 1/2003 |
| EP | 726304 | 3/1997 |
| EP | 786820 | 7/1998 |
| EP | 1 073 993 | 11/2002 |
| GB | 1416603 | 12/1975 |
| JP | 10158938 | 6/1998 |
| WO | 03/016599 | 2/2003 |

OTHER PUBLICATIONS

Dynamic Scaling, Island Size Distribution, and Morphology in the Aggregation Regime of Submonolayer Pentacene Films http://www.ee.princeton.edu/~kahnlab/publications/PRL91-136102.pdf.

Pentacene ultrathin film formation on reduced and oxidized Si surfaces http://www.ee.princeton.edu/~kahnlab/publications/PRB67-125406.

Physisorption-like Interaction at the Interfaces Formed by Pentacene and Samarium http://www.ee.princeton.edu/~kahnlab/publications/192.pdf.

Orientation of pentacene films using surface alignment layers and its influence on thin film transistor characteristics http://www.uvm.edu/~rheadric/Reprints/Swiggers2001.pdf.

(Continued)

Primary Examiner—James O Wilson
Assistant Examiner—Ebenezer Sackey

(57) ABSTRACT

The present application discloses methods for the production of organic compounds comprising a linear series of five fused carbon rings. Such compounds are useful in the production of electronic components, devices and materials. For example the methods disclosed permit the production of 2,9- and 2,10-disubstituted pentacene compounds that present particularly advantageous properties for the manufacture of semiconductor materials, and may be used in devices such as for example thin film transistors and solar cells. Also disclosed are compounds that are excellent candidates for use in the manufacture of semiconductor materials, and other components of electronic systems, by virtue of their solubility, crystal packing geometries, and electronic properties.

25 Claims, No Drawings

OTHER PUBLICATIONS

The Vibrational Reorganization Energy in Pentacene: Molecular Influences on Charge Transport http://www.ee.princeton.edu/~kahnlab/publications/194.pdf.

Synthesis and Application of Pentacene Precursor in OTFT http://www.mrc.utexas.edu/NSFWorkshop/Presentations/afzalil.pdf.

Doped Pentacene Yields Efficient Plastic Solar Cells http://www.photonics.com/spectra/tech/XQ/ASP/techid.828/QX/read.htm.

Physicists from Lucent's Bell Labs devise organic electronics and high-speed communications circuits; win scientific awards http://www.lucent.com/press/0300/000320.bla.html or http://www.globaltechnoscan.com/29march-4thapril/lucent.htm.

Flexible Electronics: On the Brink of a Tech Revolution http://dom.semi.org/web/wmagazine.nsf/0/8a7b262af0f00f8c88256afb0080dffe?OpenDocument.

The Pentacene Project http://www.research.ibm.com/leem/pentacene.html.

Organic Electronics http://www.findarticles.com/cf_0/m3125/10_72/62657296/print.jhtml.

IBM Scientists Take Significant Step Toward Production of Flexible Electronics http://www.findarticles.com/cf_0/mOWVI/2000_Nov_6/66810932/print.jhtml.

Characteristics of pentacene-based thin-film transistors Author(s): J.H. Park; C.H. Kang; Y.J. Kim; Y.S. Lee; J.S. Choi Source: Materials Science and Engineering: C (Elsevier Science) Year: 2004 vol. 24 No. 1 pp. 27-29.

Optical Properties of Solid Pentacene Author(s): K. Kim; Y.K. Yoon; M.-O. Mun; S.P. Park; S.S. Kim; S. Im; J.H. Kim Source: Journal of Superconductivity: Incorporating Novel Magnetism (Kluwer Academic Publishers) Year: 2002 vol. 15 No. 6 pp. 595-598.

Solid-state dye-sensitized photocell based on pentacene as a hole collector Author(s): G.K.R. Senadeera; P.V.V. Jayaweera; V.P.S. Perera; K. Tennakone Source: Solar Energy Materials and Solar Cells (Elsevier Science) Year: 2002 vol. 73 No. 1 pp. 103-108.

An STM investigation of the interaction and ordering of pentacene molecules on the Ag/Si(111)- (3x 3)R30 surface Author(s): P. Guaino; A.A. Cafolla; D. Carty; G. Sheerin; G. Hughes Source: Surface Science (Elsevier Science) Year: 2003 vol. 540 No. 1 pp. 107-116.

Raman phonon spectra of pentacene polymorphs Author(s): A. Brillante; R.G. Della Valle; L. Farina; A. Girlando; M. Masino; E. Venuti Source: Chemical Physics Letters (Elsevier Science) Year: 2002 vol. 357 No. 1 pp. 32-36.

Identification of polymorphs of pentacene Author(s): C.C. Mattheus; A.B. Dros; J. Baas; G.T. Oostergetel; A. Meetsma; J.L. de Boer; T.T.M. Palstra Source: Synthetic Metals (Elsevier Science) Year: 2003 vol. 138 No. 3 pp. 475-481.

Anisotropy of the mobility of pentacene from frustration Author(s): G.A. de Wijs; C.C. Mattheus; R.A. de Groot; T.T.M. Palstra Source: Synthetic Metals (Elsevier Science) Year: 2003 vol. 139, No. 1 pp. 109-114.

High-mobility low-threshold-voltage pentacene thin-film transistors prepared at rapid growth rates by pulsed-laser deposition Author(s): A. J. Salih; J. M. Marshall Source: Philosophical Magazine Letters (Taylor and Francis Ltd) Year: 1997 vol. 75 No. 3 pp. 169-177.

Pentacene self-aggregation at the Au(110)-(1x2) surface: growth morphology and interface electronic states Author(s): C. Menozzi; V. Corradini; M. Cavallini; F. Biscarini; M.G. Betti; C. Mariani Source: Thin Solid Films (Elsevier Science) Year: 2003 vol. 428 No. 1 pp. 227-231.

Electrical characteristics of pentacene-based Schottky diodes Author(s): Y.S. Lee; J.H. Park; J.S. Choi Source: Optical Materials (Elsevier Science) Year: 2003 vol. 21 No. 1 pp. 433-437.

Spin-orbit coupling and luminescence characteristics of conjugated organic molecules. I. Polyacenes Author(s): Y.F. Pedash; O.V. Prezhdo; S.I. Kotelevskiy; V.V. Prezhdo Source: Journal of Molecular Structure: Theochem (Elsevier Science) Year: 2002 vol. 585 No. 1 pp. 49-59.

Afzali, A., et al., *J. Am. Chem. Soc., 2002*, 124, 8812.

Afzali, A., et al., *Adv. Mater.*, 2003, 15, 2066.

Anthony J.E. et al. *Org Lett* (2002) 4, 15.

Aubry, J.-M.; Pierlot, C.; Rigaudy, J.; Schmidt, R. *Acc. Chem. Res.* 2003, 36, 668.

Collins, S.K., et al., *Angew. Chem.* Int. Ed., 2000, 39, 385.

Collins, S.K., et al., *Org. Lett.*, 2000, 2, 3185.

Collins, S.K., et al., *Org. Lett.*, 2002, 4, 11.

Cory, R. M.; McPhail, C. L.; Dikmans, A. J. *Tetrahedron Lett.* 1993, 34, 7533.

Danishefsky, S. J.; Kitahara, T.; Yan, C. F.; Morris, J. *J. Am. Chem. Soc.* 1979, 101, 6996.

Danishefsky, S. J.; Yan, C. F.; Singh, R. K.; Gammill, R. B.; McCurry, P.; Fritsch, N.; Clardy, J. C. *J. Am. Chem. Soc.* 1979, 101, 7001.

Gelinck, G.H. et. al.,*Nature Materials*, 2004, 3, 106.

Goodings E.P. et al. *J Chem Soc*, Perkin 1(1972), 1310.

Hendrickson, J. B.; Bergeron, R. *Tetrahedron Lett..* 1973, 14, 4747.

Heuft, M.A., et al., *Org. Lett.*, 2001, 3, 2883.

Heuft, M.A., Fallis, G., *Angew. Chem. Int. Ed.*, 2002, 41, 4520.

Heuft, M.A., et al., *Org. Lett.*, 2003, 5, 4245.

Ito, K. et al., *Angew. Chem. Int. Ed.*, 2003, 42, 1159.

Katz H.E. et al. *Acc Chem Res* (2001), 34, 359.

Li, G., Shinar, J., *App. Phys. Lett.*, 2003, 83, 5359.

Meyer zu Heringdorf F.-J. et al. *Nature* (2001) 412, 517.

Morris, J.L. et al., *J. Org. Chem.*, 1994, 59, 6484.

Randić M. *Chem Rev* (2003) 103, 3449.

Schuster, I. I.; Craciun, L.; Ho, D. M.; Pascal, R. A. Jr. *Tetrahedron*, A crystal structure of a related endoperoxide was recently published, 2002, 58, 8875.

Schleyer P.R. et al. *Org Lett* (2001) 3, 3646.

Takahashi, T., et al., *J Am. Chem. Soc.*, 2000, 122, 12876.

\* cited by examiner

COMPOUNDS COMPRISING A LINEAR SERIES OF FIVE FUSED CARBON RINGS, AND PREPARATION THEREOF

CROSS REFERENCE TO RELATED APPLICATION

This application claims the priority right of prior U.S. patent application Ser. No. 60/571,940 filed on May 18, 2004 by applicants herein.

FIELD OF THE INVENTION

The present invention relates to the field of pentacene compounds. More specifically, the present invention relates to compounds comprising a linear series of five fused carbon rings (e.g. 2,9- and 2,10-disubstituted pentacenes), their production and use in semiconductor materials and organic thin film electronic devices.

BACKGROUND TO THE INVENTION

Semiconductors are materials that have electronic properties between electrical insulators and electrical conductors. The efficiency of a semiconducting material is determined by how easily the electrons and electron 'holes' can move through the material—i.e. the electron and hole mobilities ($\mu_e$ or $\mu_h$). Highly conjugated organic compounds have overlapping atomic orbitals that form valence and conducting bands similar to metals. Organic semiconductors do not have the same electron or hole mobilities as single-crystalline silicon, but they are advantageous during fabrication as solution processing techniques such as lithography can be used.

Silicon and gallium arsenide semiconductors, silicon dioxide insulators, and metals such as aluminum and copper have dominated the semiconductor industry for many years. More recently, however, organic thin-film transistors (OTFTs) have presented an alternative to the traditional thin-film transistors based on inorganic materials. For example, research efforts have focused on linear acenes (including tetracene and pentacene), thiophene oligomers (including α-sexithiophene), regioregular polythiophenes, copper phthalocyanines and naphthalenebisimides as candidates for organic semiconductors (Katz H. E. et al. Acc Chem Res (2001), 34, 359). Of these, pentacene exhibits the best electron and hole mobilities. Charge-carrier mobility values of 1.5 $cm^2V^{-1}s^{-1}$, on/off current ratios greater than $10^8$, and sub-threshold voltages of less than 1.6 V have been reported for pentacene-based transistors. Therefore, the charge-carrier mobility values for pentacenes are comparable or even superior to those of amorphous silicon-based devices.

A rapid two-step synthesis for pentacene was reported in 1972, as shown in Scheme 1, and pentacene was found to be both light and air sensitive (Goodings E. P. et al. *J Chem Soc, Perkin I* (1972), 1310). However, more problematic is the virtual insolubility of pentacene in common organic solvents, thereby preventing solution-based processing (Mayer zu Heingdorf F.-J. et al. *Nature* (2001) 412, 517). As a result, pentacene must generally be deposited from the vapor phase by vacuum sublimation in order to achieve maximum performance. The vacuum sublimation method, however, requires expensive equipment and lengthy pump-down cycles.

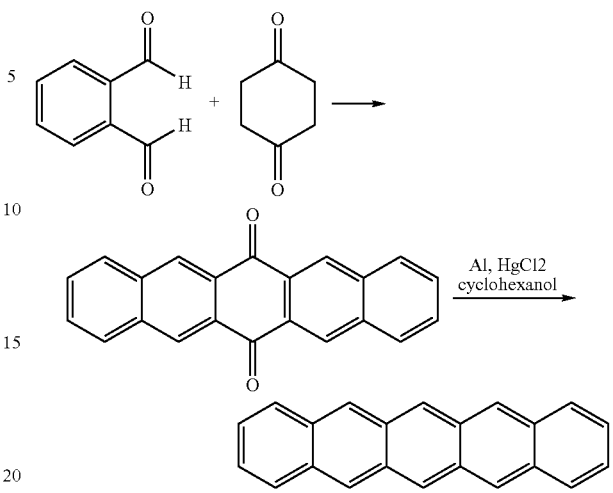

Scheme 1: Synthesis of Pentacene

Another disadvantage of pentacene relates to its polymorphic nature, which can have a detrimental influence upon the performance and reproducibility of pentacene-based devices. The alignment or structural order of the pentacene molecules differs for each polymorph or crystallographic phase, and this structural order determines the electronic properties of the device. The crystallographic phase adopted by pentacene depends on the method and conditions under which the crystals are formed. For example, when pentacene is vapor-deposited onto a substrate, a thin film phase is formed. This thin film phase is more effective at transporting charge than pentacene's bulk or single crystal phase, but it is meta-stable. For example, the thin film form of pentacene can be converted to the bulk phase by exposure to solvents such as isopropanol, acetone or ethanol.

More recently, substituted pentacene compounds have been developed that are more soluble in organic solvents, exhibit regular crystal packing, and are better suited for organic processing. For example, corresponding international patent publications WO03/028125, and WO03/027050, both published Apr. 3, 2003 and which are incorporated herein by reference, disclose substituted pentacene compounds and methods for their preparation. The substitutions include electron-donating groups and halogen atoms. Such petancene compounds are, at least in preferred embodiments, suited for use in organic semiconductor materials. Particularly useful semiconductor compounds include 2,9- and 2,10-disubstituted pentacenes, which are predicted to exhibit excellent solubility, solid-state packing and Σ-orbital overlap (Anthony, J. E. et al. *J Am Chem Soc* (2001), 123, 9482; Anthony J. E. et al. *Org Lett* (2002) 4, 15).

To date, the production of 2,9- and 2,10-disubstituted pentacenes has been difficult to achieve. International patent publication WO03/027050 discloses a method for preparing pentacene derivatives comprising the step of cyclizing at least one substituted bis(benzyl)phthalic acid to form the corresponding substituted pentacenedione by using an acid composition comprising trifluoromethanesulphonic acid, wherein the bis(benzyl)phthalic acid is selected from:

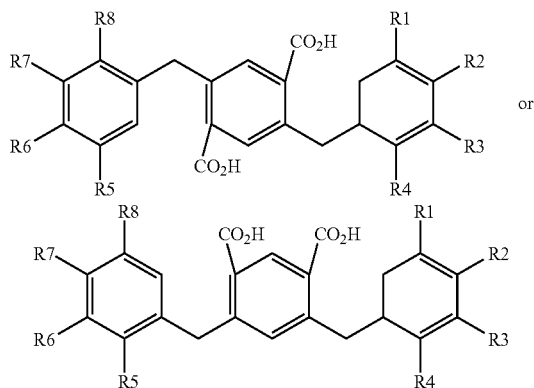

each R representing an electron-donating group, a halogen atom, or a hydrogen atom. In preferred embodiments, the method is suitable for generating a 2,9- or 2,10-disubstituted pentacene 5,7 or 5,12-dione, which can undergo reduction and dehydration to generate the corresponding disubstituted pentacene.

There remains a continuing need to develop novel pathways for the production of compounds comprising a linear series of five fused carbon rings, such as for example 2,9- and 2,10-disubstituted pentacene compounds, and corresponding pentacene derivatives. Moreover, there remains a need to develop methods that are better suited for large-scale production of a broad range of pentacene derivatives, and other compounds comprising a linear series of five fused carbon rings, within minimal cost. New pathways are desired to present opportunities to develop new classes of pentacene derivatives, for example with alternative substitutions either on the A and E rings, or the other rings of the five fused carbon ring core structure.

SUMMARY OF THE INVENTION

It is one object of the present invention, at least in preferred embodiments, to provide a method for producing compounds comprising a core structure including a linear series of five fused carbon rings.

It is another object of the present invention, at least in preferred embodiments, to provide intermediates suitable for use in the production of pentacene derivatives with one or more substitutions on the A and/or the E rings.

It is another object of the present invention, at least in preferred embodiments, to provide compounds suitable for use in electronic devices, for example in thin film transistors, or for other use as a semiconductor, or for use in inkjet fabrication.

It is another object of the present invention to provide novel compounds comprising a linear series of five fused carbon rings including, but not limited to, novel pentacenes.

Through significant inventive ingenuity, the inventors of the present invention have developed novel methods for the synthesis of organic compounds comprising for example a linear series of five fused carbon rings. Such compounds may include, but are not limited to, anthradiquinones and pentacenes. The methods of the present invention permit facile access to a broad range of compounds comprising the aforementioned five-fused carbon ring core. Such compounds include, for example, pentacenes, which may include a broad range of substituents. For example, the inclusion of acetylene groups (or at least substitutions comprising acetylene linkers) on the A and E rings affords access to compounds that are particularly suited to electronic applications. Moreover, such compounds are amenable to further manipulation, for example to custom design pentacenes having optimal electronic properties. The novel compounds of the present invention are suitable for use in the manufacture of numerous types of electronic devices, including for example thin film transistors and solar cells.

In one aspect the present invention provides for a method for the preparation of a compound comprising at least one linear series of five fused carbon rings, the method comprising the steps of:
(a) providing an unsubstituted or substituted 1,4,5,8-anthradiquinone;
(b) providing an unsubstituted or substituted acyclic, cyclic, or heterocyclic diene;
(c) performing a double or stepwise cycloaddition reaction between the 1,4,5,8-anthradiquinone and the diene to generate a core structure comprising five fused carbon rings sequentially identified as rings A, B, C, D, and E.

Preferably, the method further comprises the steps of:
(d) performing a ring opening reaction to convert a bridged form of each of rings A and E to an unbridged form; and
(e) optionally performing an aromatization reaction or equivalent on the A, and E rings of the core structure;

wherein steps (d) and (e) can be performed in any order.
Preferably, the method further comprises the step of:
(d) replacing or adding selected substituents.
Preferably, the method further comprises the step of:
(d) subjecting the compound to reducing conditions to generate a corresponding unsubstituted or substituted pentacene.

Preferably, the method generates isomeric products, and the method further comprises the step of:
(d) separating the isomeric products.
Preferably, the method further comprises the step of:
(d) performing a coupling reaction to link two or more core structures.

It should be noted that any of the additional steps (d) and/or (e) described above can be added to the basic methods of the invention. Moreover, any two or more additional steps can be performed in any order.

Preferably in step (a) the 1,4,5,8-anthradiquinone has the general formula I:

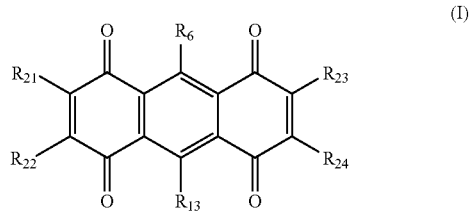

Preferably, in the compounds of formula I, each R group is independently selected from the group consisting of hydrogen, an electron-withdrawing group, and halogen.

Preferably in step (b) the diene compound has the general formula IIa or IIb:

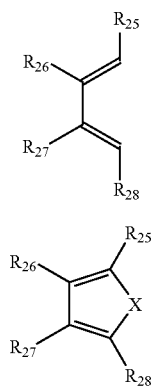

(IIa)

(IIb)

wherein each R group is H or any group that does not interfere with the capacity of the diene to undergo a cycloaddition reaction with 1,4,5,8-anthradiquinone, and X is C, O, S, or N.

Preferably, step (c) comprises a double Diels-Alder reaction between the anthradiquinone and two diene molecules.

Preferably in step (b) $R_{26}$ or $R_{27}$ comprises A-B, wherein A is a protective group, and B is a group to be protected, and wherein the method generates an compound of the formula III:

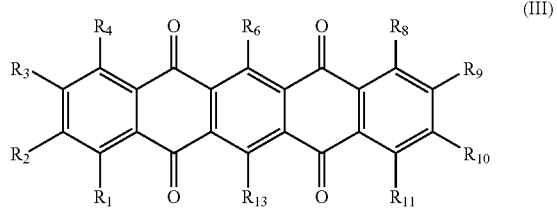

(III)

wherein $R_2$, and $R_9$ or $R_{10}$ are A-B, and each remaining R is each independently unsubstituted or substituted. More preferably, the method further comprises replacing each A-B at $R_2$, and $R_9$ or $R_{10}$ with an alternative substituent.

Preferably, when the methods of the invention involve reduction, the step of reduction generates a pentacene compound of formula IV:

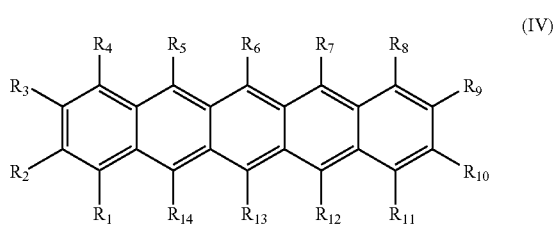

(IV)

wherein $R_2$, and $R_9$ or $R_{10}$ are A-B, and each remaining R is each independently unsubstituted or substituted. More preferably, such methods further comprise replacing each A-B at $R_2$, and $R_9$ or $R_{10}$ with an alternative substituent. More preferably, $R_2$, and $R_9$ or $R_{10}$ comprise an unsubstituted or substituted group selected from acetylene, alkyl, aryl, heteroaryl, alkenyl, and alkynyl. Most preferably, $R_2$ and $R_9$ or $R_{10}$ comprise acetylene or a linker comprising one or more triple bonds, optionally substituted by halogen and/or triflate.

Preferably, when the methods of the invention comprise coupling, the methods generate a oligomeric compound comprising multiple units of said core structure linked by acetylene groups at the 2, and 9 or 10 positions.

In accordance with the methods of the invention, preferably each A-B comprises $Si(R_{30}, R_{31}, R_{32})$ wherein each of $R_{30}, R_{31}, R_{32}$ are independently selected from any group that in conjunction with Si acts to provide a protective group. More preferably, each A-B comprises TMS, TES, TBS, TIPS, diphenyl tertiary butyl, OSi, OH, OTf, OTs, OMs, ONs, NSi, acetylene, phthalocyanine as a metal complex or free ligand, fullerene, Buckminsterfullerene $C_{60}R_{100}$, wherein $R_{100}$ is hydrogen or any substituent, or fullerene linked to the pentacene core via acetylene, or Buckminsterfullerene $C_{60}R_{100}$ linked to the pentacene core via acetylene, or phthalocyanine as a metal complex or free ligand linked to the pentacene core via acetylene. Indeed, without wishing to be bound by theory it is considered that phthalocyanine pentacenes generated in accordance with the present invention may be particularly suited for use in solar cell or solar panels, or components thereof.

Most preferably, each B is O, S, Se, or N.

Preferably, when the methods of the invention comprise the step of replacing or adding selected substituents, each A-B is replaced with Tf-O, halogen, or a substituent comprising a metal atom selected from Al, B, Cu, Co, Cr, Fe, Li, Mg, Ni, Pd, Pt, Si, Sn, Ti, and Zn. More preferably, the method further comprises replacing each Tf-O with an acetylene group, or a group comprising a linker comprising one or more triple bonds.

Preferably, when the methods of the invention comprise the separation of isomeric products, the step of separating comprises high performance liquid chromatography or fractional crystallization.

Preferably, in the diene compounds of formula IIa or IIb, $R_{25}$ is a leaving group comprising OAlk, NAlk, or halide wherein each Alk comprises an alkyl group of from 1 to 12 carbon atoms.

In another aspect, the present invention provides for a method for the preparation of a pentacene comprising substitutions at least at the 2 positions, and the 9 or 10 position, the method comprising the steps of:

(a) performing a stepwise or double Diels-Alder reaction by reacting a compound of formula IIa or IIb:

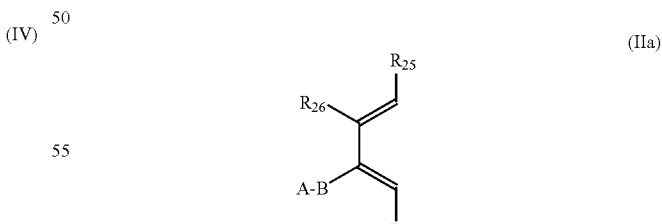

(IIa)

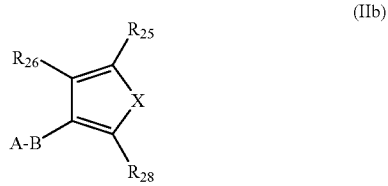

(IIb)

wherein A is a protective group, B is a group to be protected, and each R group is independent selected from H or a substituent, with a compound of formula I:

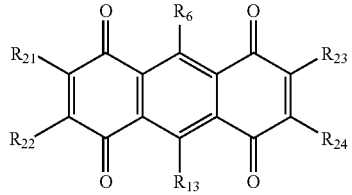

(I)

wherein each R group is independently selected from H or a substituent, and if necessary (b) optionally performing a ring opening reaction to covert a bridged form of each of rings A and E, to an unbridged form; and (c) optionally performing an aromatization reaction or equivalent on the A, and E rings of the core structure;

wherein the method generates a mixture of compounds of formula V and VI:

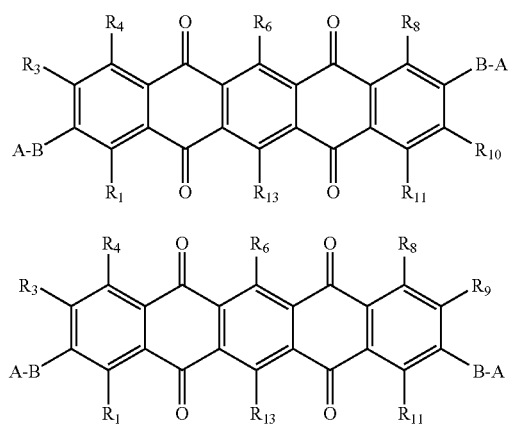

wherein A is a protective group, B is a group to be protected, and each R group is independent selected from H or a substituent.

Preferably, the method further comprises the step of:

(c) separating the compounds of formula (V) and formula (VI), and selecting the compound of formula (V) and/or the compound of formula (VI) for further processing.

Preferably, the method further comprises the step of:

(c) replacing each A or each A-B with an alternative substituent, with or without a linker comprising one or more triple bonds to form a 2,9- and/or a 2,10-disubstituted diquinone Preferably, the method further comprises the step of:

(c) subjecting the 2,9- and/or the 2,10-disubstituted diquinone to reducing conditions to generate a pentacene substituted at least in the 2 position, and the 9 or 10 position.

In another aspect, the present invention provides for a compound of the formula III:

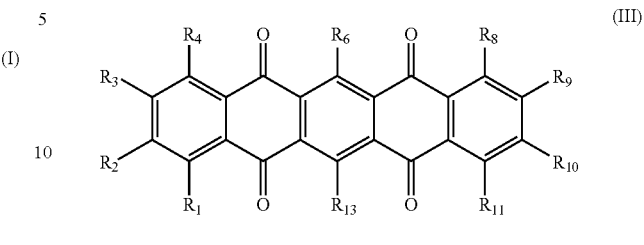

(III)

wherein R1 to R14 are each independently unsubstituted or substituted.

Preferably, the compound of formula III comprises at least one substituent on each of the A and E rings of the core structure. More preferably, the compound comprises at least one substituent on each of the A and E rings, and at least one substituent on at least one of the B, C, or D rings of the core structure. More preferably, the compound comprises substituents at least at the 2, and the 9 or 10 positions. Most preferably, the substituents at the 2, and the 9 or 10 positions are acetylene groups, or are each attached to the core structure via a linker comprising one or more triple bonds. Preferably, in accordance with the compound of formula III each substituent is independently selected from hydroxyl, alkyl, alkoxy, alkenyl, alkynyl, aryl, heteroaryl, acetylene, halogen, and triflate. More preferably, each substituent is substituted by alkyl or halogen.

In another aspect, the present invention provides for a compound of formula IV:

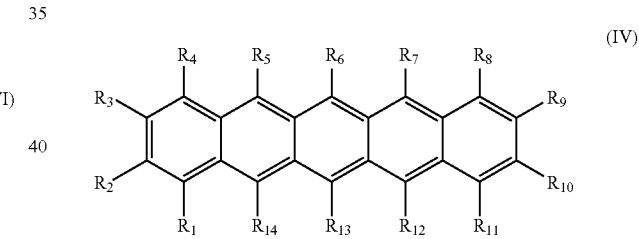

(IV)

wherein R1 to R14 are each independently unsubstituted or substituted.

Preferably, the compounds of formula IV include the proviso that the compounds of formula IV exclude pentacenes comprising alkyl groups at $R_2$ and $R_9$ and/or $R_{10}$.

Preferably, the compounds of formula IV include the proviso that when at least one of $R_1$, $R_2$, $R_3$, $R_4$, $R_8$, $R_9$, $R_{10}$, and $R_{11}$ are substituted with an electron-donating substituent, or a halogen, then the compound must include at least one further substituent at $R_5$, $R_6$, $R_7$, $R_{12}$, $R_{13}$, or $R_{14}$.

Preferably, the compound of formula IV comprises at least one substituent on each of the A and E rings of the core structure. More preferably, the compound comprises at least one substituent on each of the A and E rings, and at least one substituent on at least one of the B, C, or D rings of the core structure. More preferably, the compound comprises substituents at least at the 2, and the 9 or 10 positions. Most preferably, the substituents at the 2, and the 9 or 10 positions are acetylene groups, or are each attached to the core structure via a linker comprising one or more triple bonds. Preferably, in accordance with the compound of formula III each substituent is independently selected from hydroxyl, alkyl, alkoxy, alkenyl, alkynyl, aryl, heteroaryl, acetylene, halogen, and triflate. More preferably, each substituent is substituted by alkyl or halogen.

In another aspect, the present invention provides for the use of a compound according to formula III in the manufacture of a material suitable for use in ink-jet fabrication or as a component of an electronic device. Preferably the use is for the manufacture of a component selected from the group consisting of an Organic Thin Film Semiconductor (OTFS), an Organic Field-Effect Transistor (OFET), an Organic Light Emitting Diode (OLED), a solar cell, and a component for solar energy conversion.

In another aspect, the present invention provides for the use of a compound according to formula IV in the manufacture of a material suitable for use in ink-jet fabrication or as a component of an electronic device. Preferably the use is in the manufacture of a component selected from the group consisting of an Organic Thin Film Semiconductor (OTFS), an Organic Field-Effect Transistor (OFET), an Organic Light Emitting Diode (OLED), a solar cell, and a device for solar energy conversion.

Preferably the compound of formula IV is suitable for use as a semiconductor.

In another aspect the present invention provides for semiconductor material derived from processing of the compound of formula III.

In another aspect the present invention provides for an electronic device comprising a component selected from an Organic Thin Film Semiconductor (OTFS), an Organic Field-Effect Transistor (OFET), an Organic Light Emitting Diode (OLED), a solar cell, and a component for solar energy conversion, wherein said component comprises the semiconductor material derived from processing the compound of formula III.

In another aspect, the present invention provides for an electronic device comprising the semiconductor material derived from processing the compound of formula III.

In another aspect the present invention provides for semiconductor material derived from processing of the compound of formula IV.

In another aspect the present invention provides for an electronic device comprising a component selected from an Organic Thin Film Semiconductor (OTFS), an Organic Field-Effect Transistor (OFET), an Organic Light Emitting Diode (OLED), a solar cell, and a component for solar energy conversion, wherein said component comprises the semiconductor material derived from processing the compound of formula IV.

In another aspect, the present invention provides for an electronic device comprising the semiconductor material derived from processing the compound of formula IV.

DEFINITIONS

Numbering scheme for pentacenes: Compounds with fused aromatic ring systems are commonly given a numbering sequence in which each carbon atom that is amenable to substitution is numbered. (See, for example, James E. Banks, NAMING ORGANIC COMPOUNDS: A PROGRAMMED INTRODUCTION TO ORGANIC CHEMISTRY, Saunders College Publishing, p. 124, PA (1976).) The numbering sequence that is generally used for pentacene, for example, is shown below.

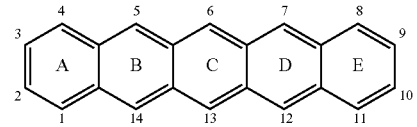

The location of a substituent on such a compound is commonly specified by reference to the number of the carbon atom to, which the substituent is bonded. There is one hydrogen atom bonded to each numbered carbon atom if no substituent is indicated. In general, the rings are identified by a letter A, B, C, and so on as shown above.

Linear Series of Five Fused Carbon Rings:

This expression refers to all compounds comprising a core structure having five fused carbon rings arranged in a linear series. Such compounds include, but are not limited to anthradiquinones, and pentacenes. Each ring of such compounds may independently be saturated, unsaturated, or aromatic, and be unsubstituted or substituted.

For convenience, the numbering scheme for substituents of all compounds comprising a linear series of five fused carbon rings is generally based upon the pentacene core structure (as discussed above) throughout this specification. However, renumbering of corresponding R groups on products (compared to corresponding substrates) does not necessarily infer that the substituent has been replaced.

Reduction/Reducing Conditions:

The term "reduction" or "reducing conditions" refers to any form of reaction that results in (i) the acceptance of one or more electrons by an atom or ion, (ii) the removal of oxygen from a compound, or the addition of hydrogen to a compound. In the context of this application, the terms further encompass reactions involving alcohols such as, for example, Grignard reactions, including for example reduction/addition to carbonyl to generate an alcohol. The terms include addition to generate an alcohol intermediate, which may be followed by aromatization.

Protective Group:

This expression encompasses any form of protective group, including for example those described in Green, T. W. and Wuts P. G. M., "Protective Groups in Organic Synthesis" ($3^{rd}$ ed. 1999) published by John Wiley ad Sons Inc. Preferably, the protective groups of the present invention are encompassed by A-B, wherein A is a protective group and B is a group to be protected. A-B can include, but is not limited to, OSi, OH, OTf, OTs, OMs, ONs, NSi, and acetylene groups, or groups comprising a linker have at least one triple carbon-carbon bond. A-B therefore includes OH (wherein H can be considered a form of "protecting group"). In preferred embodiments, when B (the group to be protected) includes O or N then A can be silyl, hydrogen or sulfonate alkyl, perfluoroalkyl, or aryl. In other preferred embodiments, where B includes a carbon or hetero atom, then A can be silyl, hydrogen or sulfonate alkyl, perfluoroalkyl or aryl.

Preferred/Preferably:

Unless otherwise stated, the terms "preferred" and "preferably" refer only to preferred features or aspect of the invention over the broadest embodiments of the invention.

Acetylene:

Acetylene groups encompass, at least in preferred embodiments, any group comprising at least one triple carbon bond, or a group comprising a linker comprising at least one triple carbon bond.

Additional Chemical Terms

The term "carbo", "carbyl," "hydrocarbo," and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring halide) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein at least one of said ring(s) is aromatic.

The term "heterocyclic," as used herein, pertains to cyclic compounds and/or 10 groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., 15 fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one preferred embodiment, the substituent(s) are independently selected from: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s) are independently selected from:
—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBU)$_2$, and —N(tBu)$_2$;
—CN;
—NO$_2$;
-Me, -Et, -nPr, -iPr, -nBu, -tBu; —CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, CH$_2$CH$_2$NH$_2$, and —CH$_2$CH$_2$NMe$_2$; and,
optionally substituted phenyl.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (also carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, cyclohexyl, and norbornane, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$) isopropenyl (—C(CH$_3$)=CH$_2$), butenyl, pentenyl, and hexenyl.

Examples of (unsubstituted) unsaturated $C_{1-7}$alkyl groups which have one or more carbon-carbon triple bonds (also referred to as "$C_{2-7}$alkynyl" groups) include, but are not limited to, ethynyl, and 2-propynyl (propargyl).

Examples of unsaturated alicyclic (also carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Additional examples of substituted $C_{3-7}$cycloalkyl groups include, but are not limited to, those with one or more other rings fused thereto, for example, those derived from: indene ($C_9$), indan (2,3-dihydro-1H-indene) ($C_9$), tetraline (1,2,3,4-tetrahydronaphthalene ($C_{10}$), adamantane ($C_{10}$), decalin (decahydronaphthalene) ($C_{12}$), fluorene ($C_{13}$), phenalene ($C_{13}$). For example, 2H-inden-2-yl is a $C_5$cycloalkyl group with a substituent (phenyl) fused thereto.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms.

For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$) piperidine ($C_6$) dihydropyridine ($C_6$), tetrahydropyridine ($C_6$), azepine ($C_7$);

—$O_1$: oxirane ($C_3$) oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_6$), and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$ aryl: The term "$C_{5-20}$ aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. This particularly applied to substituents of the pentacene core of the compounds generated in accordance with the present invention.

For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), pyrene ($C_{16}$), and fullerenes particularly for example $C_{60}$ ("Bucky Ball") such as $C_{60}H$ or $C_{60}R_{100}$, wherein $R_{100}$ represents any substituent, particularly those discussed herein. Indeed, 2,9 and 2,10 disubstituted pentacenes substituted with fullerene groups generate dumbbell-shaped molecules that may have particular use in specific embodiments.

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O1$), benzisoxazole ($N_1O_1$), benzodioxole (O$_2$), benzofurazan (N$_2$O$_1$), benzotriazole (N$_3$), benzothiofuran (S1), benzothiazole (N$_1$S$_1$), benzothiadiazole (N$_2$S);

C$_{10}$heterocyclic groups (with 2 fused rings) derived from benzodioxan (O$_2$), quinoline (N$_1$), isoquinoline (N$_1$), benzoxazine (N$_1$O$_1$), benzodiazine (N$_2$), pyridopyridine (N$_2$) quinoxaline (N$_2$) quinazoline (N$_2$);

C$_{13}$heterocyclic groups (with 3 fused rings) derived from carbazole (N$_1$), dibenzofuran (O$_1$), dibenzothiophene (S$_1$); and, C$_{14}$heterocyclic groups (with 3 fused rings) derived from acridine (N$_1$), xanthene (O$_1$), phenoxathiin (O$_1$S$_1$), phenazine (N$_2$) phenoxazine (N$_1$O$_1$), phenothiazine (N$_1$S$_1$), thianthrene (S$_2$), phenanthridine (N$_1$), phenanthroline (N$_2$) phenazine (N$_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substituents include, but are not limited to C$_{1-7}$alkyl, C$_{3-20}$heterocyclyl, C$_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

C$_5$: cyclopentanone, cyclopentenone, cyclopentadienone;
C$_6$: cyclohexanone, cyclohexenone, cyclohexadienone;
O$_1$: furanone (C$_5$), pyrone (C$_6$);
N$_1$: pyrrolidone (pyrrolidinone) (C$_5$), piperidinone (piperidone) (C$_6$), piperidinedione (C$_6$);
N$_2$: imidazolidone (imidazolidinone) (C$_5$), pyrazolone (pyrazolinone) (C$_5$), piperazinone (C$_6$), piperazinedione (C$_6$), pyridazinone (C$_6$), pyrimidinone (C$_6$)(e.g., cytosine), pyrimidinedione (CO (e.g., thymine, uracil), barbituric acid (C$_6$);
N$_1$S$_1$: thiazolone (C$_5$), isothiazolone (C$_5$);
N$_1$O$_1$: oxazolinone (C$_5$).

Polycyclic examples of such groups include, but are not limited to, those derived from:

C$_9$: indenedione;
N$_1$: oxindole (C$_9$);
O$_1$: benzopyrone (e.g., coumarin, isocoumarin, chromone) (C$_{10}$);
N$_1$O$_1$: benzoxazolinone (C$_9$), benzoxazolinone (C$_{10}$);
N$_2$: quinazolinedione (C$_{10}$);
N$_4$: purinone (C$_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride (C$_5$), succinic anhydride (C$_5$), and glutaric anhydride (C$_6$);

cyclic carbonates (—O—C(=O)—O— in a ring), such as ethylene carbonate (C$_5$) and 1,2-propylene carbonate (C$_5$);

imides (—C(=O)—NR—C(=O)— in a ring), including but not limited to, succinimide (C$_5$), maleimide (C$_5$), phthalimide, and glutarimide (C$_6$);

lactones (cyclic esters, —O—C(=O)— in a ring), including, but not limited to, β-propiolactone, γ-butyrolactone, δ-valerolactone (2-piperidone), and ∈-caprolactone;

lactams (cyclic amides, —NR—C(=O)— in a ring), including, but not limited to, β-propiolactam (C$_4$), γ-butyrolactam (2-pyrrolidone) (C$_5$), δ-valerolactam (C$_6$) and ∈-caprolactam (C$_7$);

cyclic carbamates (—O—C(=O)—NR— in a ring), such as 2-oxazolidone (C$_5$);

cyclic ureas (—NR—C(=O)—NR— in a ring), such as 2-imidazolidone (C$_5$) and pyrimidine-2,4-dione (e.g., thymine, uracil) (C$_6$).

The above C$_{1-7}$alkyl, C$_{3-20}$heterocyclyl, and C$_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a C$_{1-7}$alkyl group (also referred to as a C$_{1-7}$alkoxy group, discussed below), a C$_{3-20}$heterocyclyl group (also referred to as a C$_{3-20}$heterocyclyloxy group), or a C$_{5-20}$aryl group (also referred to as a C$_{5-20}$aryloxy group), preferably a C$_{1-7}$alkyl group.

C$_{1-7}$alkoxy: —OR, wherein R is a C$_{1-7}$alkyl group. Examples of C$_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ∈-caprolactone; and lactams (cyclic amides, —NH—C(=O)— in a ring), including, but not limited to, β-propiolactam, γ-butyrolactam, δ-valerolactam, and ∈-caprolactam.

Imino (imine): =NR, wherein R is an imino substituent, for example, hydrogen, C$_{1-7}$alkyl group, a C$_{3-20}$heterocyclyl group, or a C$_{5-20}$aryl group, preferably hydrogen or a C$_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$alkyl group (also referred to as C$_{1-7}$alkylacyl or C$_{1-7}$alkanoyl), a C$_{3-20}$heterocyclyl group (also referred to as C$_{3-20}$heterocyclylacyl), or a C$_{5-20}$aryl group (also referred to as C$_{5-20}$arylacyl), preferably a C$_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or Carboxy (carboxylic acid): —COOH.

Ester (carboxylate, carboxylic acid ester, oxycarbonyl): —C(=O)OR, wherein R is an ester substituent, for example, a C$_{1-7}$alkyl group, a C$_{3-20}$heterocyclyl group, or a C$_{5-20}$aryl group, preferably a C$_{1-7}$alkyl group. Examples of ester groups include, but are not limited to, —C(=O)OCH₃, —C(=O)OCH₂CH₃, —C(=O)OC(CH₃)₃, and C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH₃ (acetoxy), —OC(=O)CH₂CH₃, —OC(=O)C(CH₃)₃, —OC(=O)Ph, and —OC(=O)CH₂Ph.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)NH(CH₃)₂, —C(=O)NHCH₂CH₃, and —C(=O)N(CH₂CH₃)₂, as well as amido groups in which R¹ and R² together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR¹C(=O)R², wherein R¹ is an amide substituent, for example, a $C_{1-7}$alkyl group, a $C_{3-20}$heterocyclyl group, or a $C_{5-20}$aryl group, preferably a $C_{1-7}$alkyl group, and R² is an acyl substituent, for example, a $C_{1-7}$alkyl group, a $C_{3-20}$heterocyclyl group, or a $C_{5-20}$aryl group, preferably a $C_{1-7}$alkyl group. Examples of acylamido groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

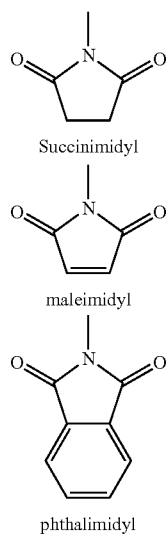

Succinimidyl maleimidyl phthalimidyl

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)NH(CH₃)₂, and —C(=S)NHCH₂CH₃.

Tetrazolyl: a five membered aromatic ring having four nitrogen atoms and one carbon atom,

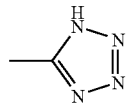

Diazine, including 1,3 diazine, pyrimidine, miazine.

Amino: —NR¹R², wherein R¹ and R² are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R¹ and R², taken together with the nitrogen atom to which they are attached, form a heterocyclic ring having from 4 to 8 ring atoms. Examples of amino groups include, but are not limited to, —NH₂, —NHCH₃, —NHCH(CH₃)₂, —N(CH₃)₂, —N(CH₂CH₃)₂, and —NHPh.

Examples of cyclic amino groups include, but are not limited to, aziridino, azetidino, piperidino, piperazino, morpholino, and thiomorpholino.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH₃ and —SCH₂CH₃Sulfonic acid (sulfo): —S(=O)₂OH.

Sulfonate (sulfonic acid ester): —S(=O)₂OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)2OCH₃ and —S(=O)2OCH₂CH₃.

Sulfone (sulfonyl): —S(=O)₂R, wherein R is a sulfone substituent, for example, a $C_{1-7}$alkyl group, a $C_{3-20}$heterocyclyl group, or a $C_{5-20}$aryl group, preferably a $C_{1-7}$alkyl group. Examples of sulfone groups include, but are not limited to, —S(=O)₂CH₃ (methanesulfonyl, mesyl), —S(=O)₂CF₃, —S(=O)₂CH₂CH₃, and 4-methylphenylsulfonyl (tosyl).

Sulfonyloxy: —OS(=O)₂R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)₂CH₃ and —OS(=O)₂CH₂CH₃.

Sulfinyl: —S=O

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH₃ and —OS(=O)CH₂CH₃.

Sulfamino: —NR¹S(=O)²OH, wherein R¹ is an amino substituent, as defined for amino groups. Examples of sulfamino groups include, but are not limited to, NHS(=O)²OH and —N(CH³)S(=O)²)H.

Sulfonamino: —NR¹S(=O)²R, wherein R¹ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH3 and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$ wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkOXY-$C_{5-20}$aryl group, e.g., as in anisole).

These and other specific examples of such substituted groups are also discussed below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a "$C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{5-20}$aryl-$C_{1-7}$alkyl: The term "$C_{5-20}$aryl-$C_{1-7}$alkyl," as used herein, describes certain $C_{1-7}$alkyl groups which have been substituted with a $C_{5-20}$aryl group. Examples of such groups include, but are not limited to, benzyl (phenylmethyl), tolylmethyl, phenylethyl, and triphenylmethyl (trityl).

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

Some substituents are bidentate, that is, have two points for covalent attachment. For example, a bidentate group may be covalently bound to two different atoms on two different groups, thereby acting as a linker therebetween. Alternatively, a bidentate group may be covalently bound to two different atoms on the same group, thereby forming, together with the two atoms to which it is attached (and any intervening atoms, if present) a cyclic or ring structure. In this way, the bidentate substituent may give rise to a heterocyclic group/compound and/or an aromatic group/compound. Typically, the ring has from 3 to 8 ring atoms, which ring atoms are carbon or heteroatoms (e.g., boron, silicon, nitrogen, phosphorus, oxygen, and sulfur, typically nitrogen, oxygen, and sulfur), and wherein the bonds between said ring atoms are single or double bonds, as permitted by the valencies of the ring atoms. Typically, the bidentate group is covalently bound to vicinal atoms, that is, adjacent atoms, in the parent group.

$C_{1-7}$alkylene: The term "$C_{1-7}$alkylene," as used herein, pertains to a bidentate moiety obtained by removing two hydrogen atoms, either both from the same carbon atom, or one from each of two different carbon atoms, of a $C_{1-7}$hydrocarbon compound having from 1 to 7 carbon atoms, which may be aliphatic or alicyclic, or a combination thereof, and which may be saturated, partially unsaturated, or fully unsaturated.

Examples of linear saturated $C_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of branched saturated $C_{1-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{1-7}$alkylene groups include, but are not limited to, —CH=CH— (vinylene), —CH=CH—CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CHCH=CH—CH$_2$—CH$_2$—, —CH=CH—CH$_2$—CH=CH—, and —CH=CH—CH$_2$—CH$_2$—CH=CH—.

Examples of branched partially unsaturated $C_{1-7}$alkylene groups include, but are not limited to, —C(CH$_3$)=CH—, —C(CH$_3$)=CH—CH$_2$—, and —CH=CH—CH(CH$_3$)—.

Examples of alicyclic saturated $C_{1-7}$alkylene groups include, but are not limited to, cyclopentylene (e.g., cyclopent-1,3-ylene), and cyclohexylene (e.g., cyclohex-1,4ylene).

Examples of alicyclic partially unsaturated $C_{1-7}$alkylene groups include, but are not limited to, cyclopentenylene (e.g., 4-cyclopenten-1,3-ylene), cyclohexenylene (e.g., 2-cyclohexen-1,4-ylene, 3-cyclohexen-1,2-ylene, 2,5-cyclohexadien-1,4-ylene).

$C_{5-20}$arylene: The term "$C_{5-20}$arylene," as used herein, pertains to a bidentate moiety obtained by removing two hydrogen atoms, one from each of two different ring atoms of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboarylene groups," in which case the group may conveniently be referred to as a "$C_{5-20}$carboarylene" group.

Alternatively, the ring atoms may include one or more heteroatoms, including but not limited to oxygen, nitrogen, and sulfur, as in "heteroarylene groups." In this case, the group may conveniently be referred to as a "$C_{5-20}$heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$arylene groups which do not have ring heteroatoms (i.e., $C_{5-20}$carboarylene groups) include, but are not limited to, those derived from benzene (i.e., phenyl) ($C_6$), naphthalene ($C_{10}$), anthracene ($C_{14}$), phenanthrene ($C_{14}$), and pyrene ($C_{16}$).

Examples of $C_{5-20}$heteroarylene groups include, but are not limited to, $C_5$heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$heteroarylene groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

$C_{5-20}$Arylene-$C_{1-7}$alkylene: The term "$C_{5-20}$arylene-$C_{1-7}$alkylene," as used herein, pertains to a bidentate moiety comprising a $C_{5-20}$arylene moiety, -Arylene-, linked to a $C_{1-7}$alkylene moiety, -Alkylene-, that is, -Arylene-Alkylene-.

Examples of $C_{5-20}$arylene-$C_{1-7}$alkylene groups include, but are not limited to, phenylene-methylene, phenylene-ethylene, phenylene-propylene, and phenylene-ethenylene (also known as phenylene-vinylene).

$C_{5-20}$Alkylene-$C_{1-7}$arylene: The term "$C_{5-20}$alkylene-$C_{1-7}$arylene," as used herein, pertains to a bidentate moiety comprising a $C_{5-20}$alkylene moiety, -Alkylene-, linked to a $C_{1-7}$arylene moiety, -Arylene-, that is, -Alkylene-Arylene-.

Examples of $C_{5-20}$alkylene-$C_{1-7}$arylene groups include, but are not limited to, methylene-phenylene, ethylene-phenylene, propylene-phenylene, and ethenylene-phenylene (also known as vinylene-phenylene).

Included in the above are the well known ionic, salt, solvate (e.g., hydrate), and protected forms of these substituents. For example, a reference to carboxylic acid (—COOH) also includes carboxylate (—COO$^-$). Similarly, a reference to an amino group includes a salt, for example, a hydrochloride salt, of the amino group. A reference to a hydroxyl group also includes conventional protected forms of a hydroxyl group. Similarly, a reference to an amino group also includes conventional protected forms of an amino group.

In particularly preferred embodiments of the invention, the term 'substituents' may include but is not limited to the group consisting of hydrogen, $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl; each optionally substituted with $C_1$-$C_5$ alkyl, halogen, $C_1$-$C_5$ alkoxy, or with a phenyl group optionally substituted with halogen, $C_1$-$C_5$ alkyl, or $C_1$-$C_5$ alkoxy, and acetylene comprising from 2 to 20 carbon atoms. In specific embodiments acetylene substituents may be particularly preferred. In other preferred embodiments, each substituent may be a metallocycles or heterocyclicmetallocycles (to include porphyrins and phthalocyaines), or perfluoroalkyl or diazine, attached either directly to the linear series of five fused carbon rings, or attached via acetylene. Each substituent is selected independently to other substituents unless otherwise indicated.

DETAILED DESCRIPTION OF THE INVENTION

Functionalized pentacene compounds with substituents on the terminal A and E rings are predicted to have better intermolecular π-stacking than compounds with substituents attached to the central C ring. However, few synthetic routes to pentacenes with substituents on the A and E rings are currently known. Pentacene has a greater electron density and reactivity at the central C ring (Schleyer P. R. et al. *Org Lett* (2001) 3, 3646; Randić M. *Chem Rev* (2003) 103, 3449) making selective functionalization of pentacene on the A and E rings difficult.

In preferred embodiments, the inventors of the present invention have developed novel pathways for the production of compounds comprising a linear series of five fused carbon rings, which are believed to present significant advantages over the methods of the prior art. Without wishing to be bound by theory, the methods of the present invention present the opportunity to manufacture, at least in preferred embodiments, alternative pentacene substitutions at the A and E rings, thereby providing a greater degree of substituent flexibility. Such substituents can be used to more carefully tune the electronic properties and/or affect the solid-state packing of the pentacene derivatives for use in electronic components such as thin-film transistors. However, the invention is not limited in this regard. The methods of the present invention permit the formation of a wide range of compounds with a core structure comprising a linear series of five fused carbon rings. The novel methods allow facile access to a wide range of compounds including substituted pentacenes and anthradiquinones that were previously unobtainable or difficult to obtain.

Such compounds include those of formula III or IV:

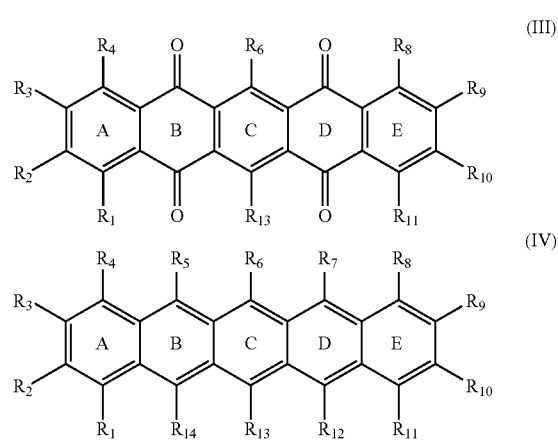

wherein R1 to R14 are each independently unsubstituted or substituted. The methods, at least in preferred embodiments, allow access to compounds comprising at least one substituent on each of the A and E rings of the core structure, or compounds comprising at least one substituent on each of the A and E rings, and at least one substituent on at least one of the B, C, or D rings of the core structure. The methods also allow access to compounds with substitutions at the 2, and the 9 or 10 positions, and other positions in the five fused carbon ring system. In most preferred embodiments, the methods of the present invention permit the production of compounds comprising a linear series of five fused carbon rings substituted with acetylene groups, or by substituents that are attached to the core structure via a linker comprising one or more triple bonds. Such compounds are amenable to further substitution or coupling via the acetylene moieties.

In one particularly preferred embodiment of the present invention there is provided a method for the preparation of an compound comprising at least one linear series of five fused carbon rings, each carbon ring being saturated, unsaturated, or aromatic, and being unsubstituted or substituted, the method comprising the steps of:

(a) providing an unsubstituted or substituted 1,4,5,8-anthradiquinone;
(b) providing an unsubstituted or substituted acyclic, cyclic, or heterocyclic diene;
(c) performing a double or stepwise cycloaddition reaction between the 1,4,5,8-anthradiquinone and the diene compound to generate a core structure comprising five fused carbon rings;
(d) optionally performing a ring opening reaction to covert a bridged form of each of rings A and E, if present, to an unbridged form;
(e) optionally performing an aromatization reaction or equivalent on the A, and E rings of the core structure;
(f) optionally replacing or adding selected substituents;
(g) optionally subjecting the compound to reducing conditions to generate a corresponding unsubstituted or substituted pentacene;
(h) optionally separating isomeric products; and
(i) optionally performing a coupling reaction to link two or more core structures;

wherein optional steps (d), (e), (f), (g), and (h), can be performed in any order.

In preferred embodiments the 1,4,5,8-anthradiquinone has the general formula I:

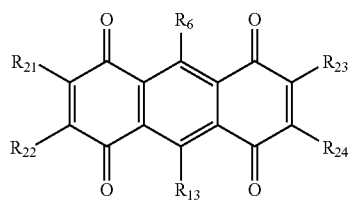

(I)

wherein each R group is independently selected from the group consisting of an electron-withdrawing group, halogen, and a protonated amine. Moreover, the diene compound has the general formula IIa or IIb:

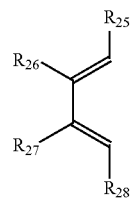

(IIa)

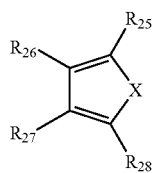

(IIb)

wherein each R group is H or any group that does not interfere with the capacity of the diene to undergo a cycloaddition reaction with 1,4,5,8-anthradiquinone, and X is C, O, S, or N. Most preferably the reaction comprises a double Diels-Alder reaction between the anthradiquinone and two diene molecules. In most preferred embodiment, $R_{25}$ may be considered a leaving group. For example, $R_{25}$ may comprise OAlk wherein each Alk comprises an alkyl group of from 1 to 12 carbon atoms, or $R_{25}$ and $R_{28}$ may be halogen.

In specific embodiments of the invention, dienes of the formula IIb such as furanones may result in the production of linear five-fused carbon ring structures in the manner shown in Scheme 1 below:

Scheme 1

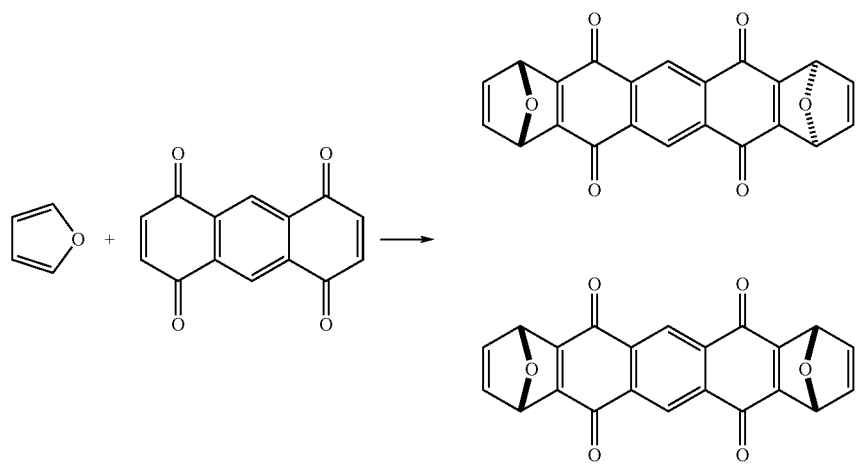

Asymmetric ring opening (ARO) of these bicyclo compounds by techniques that are well known in the art would lead to the corresponding aromatic compounds. However, such bicyclo compounds are particularly amendable to manipulation, for example by the addition or replacement of substituents, or by reduction of the ketones, before the ring opening and elimination. Asymmetric ring-opening may be conducted in the manner shown in Scheme 2 below:

Scheme 2

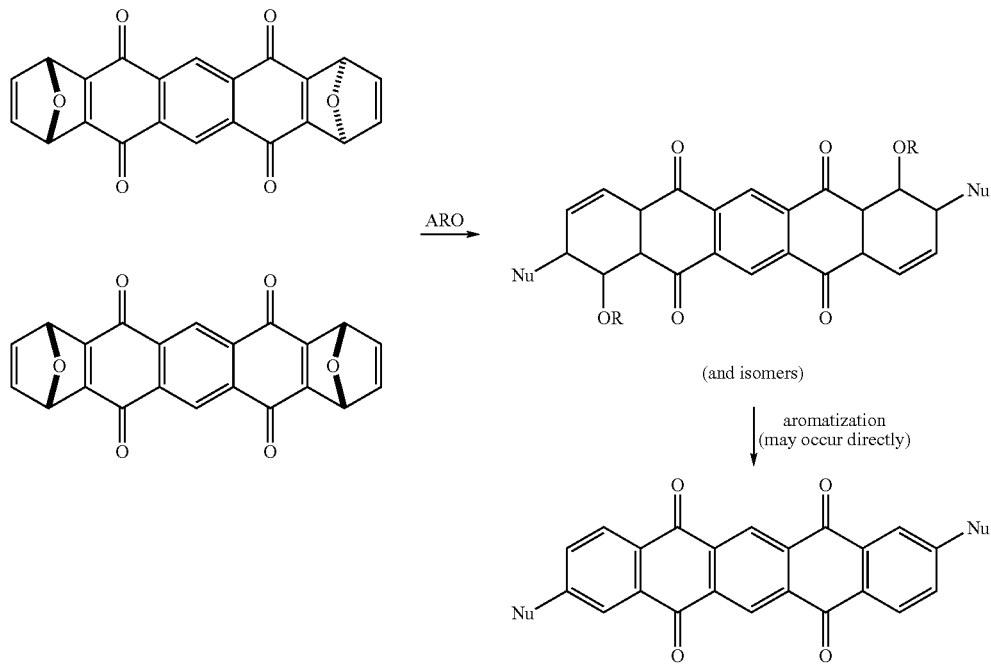

The method defined in Scheme 1 and 2 above are within the scope of the present invention, and present further opportunities for selective substituent addition to the resulting core structure of five fused carbon rings.

The methods of the present invention are specifically designed, at least in preferred embodiments, for the production of pentacene compounds with substitutions in the 2 and 9 or 10 positions. Such pentacene compounds are particularly suited for use in electronic applications by virtue of their desirable crystal packing properties (see later). For this reason, the diene compounds of formula (IIa) or (IIb) preferably comprise substituents at R26 or R27, each comprising A-B, wherein A is a protective group, and B is a group to be protected. In this way, the methods of the invention may generate compounds of the formula III:

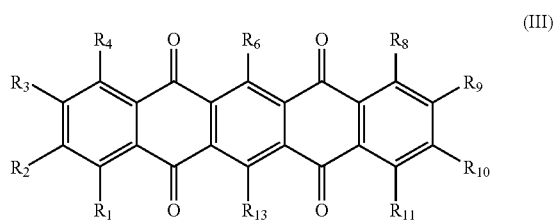

(III)

wherein R1 to R14 are each independently unsubstituted or substituted, wherein preferably at least R2 and R9 or R10 are substituted with A-B, or an alternative substituent. In this case, the substituents at R, and at R9 or R10 are derived from R26 or R27 of the diene substrates.

Moreover, optional reduction of the compound of formula III can lead to the production of pentacene compounds of formula IV:

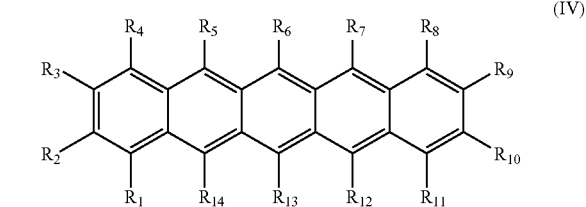

(IV)

wherein preferably, R1 to R14 are each independently unsubstituted or substituted, and wherein more preferably at least R2 and R9 or R10 are substituted with A-B, or an alternative substituent. The substituents at the R2 and R9 or R10 positions are preferably selected from acetylene, alkyl, aryl, heteroaryl, alkenyl, and alkynyl. Most preferably, R2 and R9 or R10 may comprise acetylene or a linker comprising one or more triple bonds, optionally substituted by halogen. Preferably, each A-B is a silica-based protective group. For example, each A may comprise a silyl ether such as TMS, TES, TBS, and TIPS, and each B may be O, S, Se, or N.

In another preferred embodiment, the method of the present invention may comprise step (i) as recited above, thereby to generate an oligomeric compound comprising pentacyclic units linked by acetylene groups at the 2 and 9 or 10 positions. Without wishing to be bound by theory, it is considered possible that such oligomeric chains of core structures (each core structure comprising a linear array of five fused carbon rings) may exhibit very desirable crystal packing and electronic properties by virtue of optimal ∈-orbital electron overlap. The present invention therefore encompasses oligomeric or polymeric forms of the compounds disclosed herein.

In most preferred embodiments, the methods of the present invention are for the preparation of pentacenes at least comprising substitutions at the 2, and the 9 or 10 positions, the method comprising the steps of:

(a) performing a stepwise or double Diels-Alder reaction by reacting a compound of formula IIa or IIb:

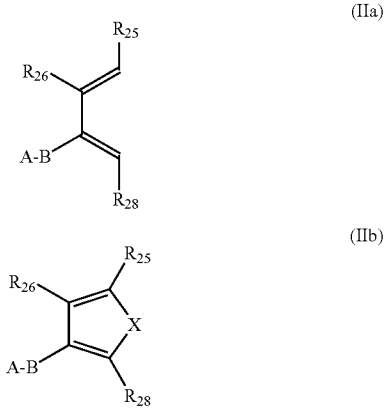

wherein A is a protective group, B is a group to be protected, each R group is independent selected from H or a substituent, and X is C, O, S, or N, with a compound of formula II:

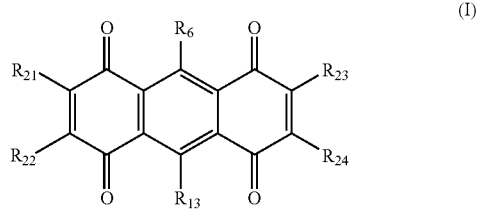

wherein each R group is independent selected from H or a substituent to form a mixture of compounds of formula V and VI:

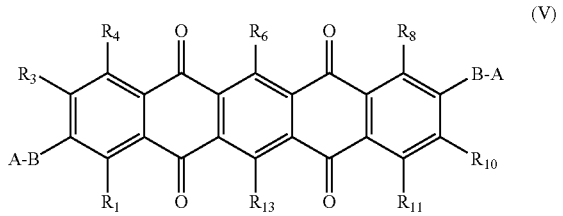

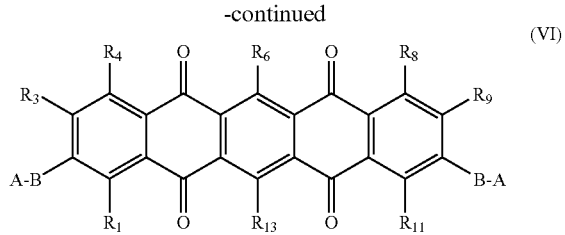

wherein A is a protective group, B is a group to be protected, and each R group is independent selected from H or a substituent;

(b) optionally separating the compounds of formula (V) and formula (VI), and selecting the compound of formula (V) and/or the compound of formula (VI) for further processing;

(c) replacing each A or each A-B with any substituent, with or without a linker comprising one or more triple bonds to form a 2,9- and/or a 2,10-disubstituted diquinone;

(d) subjecting the 2,9- and/or the 2,10-disubstituted diquinone to reducing dehydrating conditions to generate a pentacene substituted at least in the 2 position, and the 9 or 10 position.

The step of optional separation of the isomers V and VI may involve, for example, high performance liquid chromatography, fractional crystallization, or other suitable techniques that are well known in the art.

It should be noted that the diene may preferably include a protective group that will ultimately confer functionalization to the A and/or E ring of the pentacene. Any protective group may be used for this purpose in accordance with the corresponding protected group, and the protective group may be substituted as desired at a later stage. Particularly preferred protective groups include silyl ethers, which may be selected from, but not limited to, TMS, TES, TBS, or TIPS. Such protective groups can be substituted by methods known in the art. For example, diquinone compounds having only silyl ether substituents at the 2, and the 9 or 10 positions (originating from $R_{27}$ of the diene) may be subjected to desilylation and triflation to generate the compounds shown in formulae (VII) and (VIII):

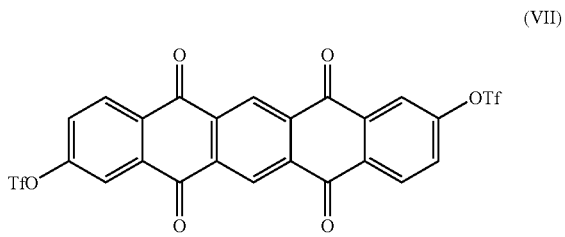

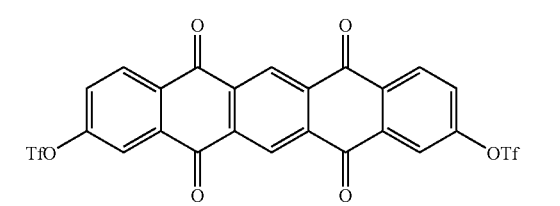

Further processing of the compounds of formula VII or VIII can be carried out, for example by coupling reactions, such as for example a Sonogashira reaction involving Pd-coupling. Subsequent reduction of the diquinone core can generate the corresponding disubstituted pentacene.

The methods of the present invention have proven highly successful and flexible in the production of 2,9- and 2,10-disubstituted pentacene compounds. Importantly, the methods of the present invention present opportunities for the production of novel 2,9- or 2,10-disubstituted pentacenes comprising acetylene substituents, which are themselves very useful as intermediates for the generation of alternative substitutions or for coupling reactions.

The present invention further encompasses a wide range of compounds that at least comprise a linear series of five fused carbon rings.

Such compounds include those of the formula III:

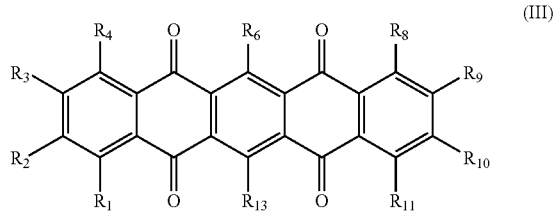

(III)

wherein R1 to R13 are each independently unsubstituted or substituted.

In preferred embodiments, the present invention provides for a compound of formula IV:

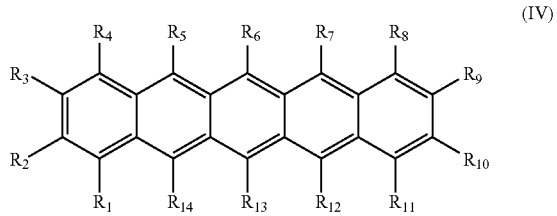

(IV)

wherein R1 to R14 are each independently unsubstituted or substituted.

Preferably, the compounds of formula IV include the proviso that the compounds of formula IV exclude pentacenes comprising only alkyl groups at $R_2$ and $R_9$ and/or $R_{10}$.

Preferably, the compounds of formula IV include the proviso that when at least one of $R_1$, $R_2$, $R_3$, $R_4$, $R_8$, $R_9$, $R_{10}$, and $R_{11}$ are substituted with an electron-donating substituent, or a halogen, then the compound must include at least one further substituent at $R_5$, $R_6$, $R_7$, $R_{12}$, $R_{13}$, or $R_{14}$.

Preferably, the compounds of formula III or IV comprise at least one substituent on each of the A and E rings of the core structure. More preferably, the compound comprises at least one substituent on each of the A and E rings, and at least one substituent on at least one of the B, C, or D rings of the core structure. More preferably, the compound comprises substituents at least at the 2, and the 9 or 10 positions. Most preferably, the substituents at the 2, and the 9 or 10 positions are acetylene groups, or are each attached to the core structure via a linker comprising one or more triple bonds. Preferably, in accordance with the compound of formula III each substituent is independently selected from hydroxyl, alkyl, alkoxy, alkenyl, alkynyl, aryl, heteroaryl, acetylene, halogen, and triflate. More preferably, each substituent is substituted by alkyl or halogen.

Without wishing to be bound by theory, the methods of the invention provide for rapid synthesis of the compounds of the invention. Importantly, the methods afford a significant degree of flexibility with regard to the substituents located on the substrates during synthesis of the five fused carbon ring core structure. Moreover, the possibility of using cyclic dienes to generate bicyclo compounds presents a further opportunity to manipulate the substituents on the core structure. The optional reduction of the anthradiquinone compounds of the invention presents further opportunities for substituent addition or replacement.

The pentacene compounds of the present invention are differentiated over those of the prior art by virtue of the wide range of possible substituents that can be positioned on the A and E rings, as well as the B, C, and D rings, and also their solubility on organic solvents. Their solubility is such that in selected embodiments the compounds of the present invention may be useful for ink jet fabrication. In one particularly advantageous embodiment, the A and E rings may comprise acetylene substituents, or may comprise substituents attached to the core structure via a linker of one or more triple bonds. This option presents unique opportunities for the provision of a wide range of substituents at such positions on the core structure, for example by manipulation or replacement of the acetylene. In further selected embodiments, the pentacene compounds of the invention may include Buckminster-fullerene-containing substituents and/or phtholocyanine substituents to generate pentacene compounds suitable for use, for example, in solar cells or components thereof.

Generation of Organic Thin Film Transistors (OTFTs) or Other Electronic Components The present invention provides methods for the production of compounds suitable for use in the manufacture of components, specifically organic semiconductor components, of Organic Thin Film Transistors and other electronic devices. The present invention encompasses such components, their manufacture, and OTFTs containing them. The methods of the present invention may be useful in the production of any types of OTFTs that incorporate pentacene derivative molecules.

Typically, a thin film transistor includes a gate electrode, a gate dielectric on the gate electrode, a source electrode and a drain electrode adjacent to the gate dielectric, and a semiconductor layer adjacent to the gate dielectric and adjacent to the source and drain electrodes. More specifically, an organic thin film transistor (OTFT) has an organic semiconductor layer. Such OTFTs are known in the art as shown, for example, in U.S. Pat. No. 6,433,359, issued Aug. 13, 2002, and U.S. Pat. No. 6,617,609 issued Sep. 9, 2003, which are herein incorporated by reference.

A substrate can be used to support the OTFT, e.g., during manufacturing, testing, storage, use, or any combination thereof. The gate electrode and/or gate dielectric may provide sufficient support for the intended use of the resultant OTFT and another substrate is not required. For example, doped silicon can function as the gate electrode and support the OTFT. In another example, one substrate may be selected for testing or screening various embodiments while another substrate is selected for commercial embodiments. In another embodiment, a support may be detachably adhered or mechanically affixed to a substrate, such as when the support is desired for a temporary purpose. For example, a flexible oligomeric substrate may be adhered to a rigid glass support, which support could be removed. In some embodiments, the substrate does not provide any necessary electrical function for the OTFT. This type of substrate is termed a "non-participating substrate" in this document.

Useful substrate materials can include organic and/or inorganic materials. For example, the substrate may comprise inorganic glasses, ceramic foils, polymeric materials, filled polymeric materials, coated metallic foils, acrylics, epoxies, polyamides, polycarbonates, polyimides, polyketones, poly (oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), and fiber-reinforced plastics (FRP).

The gate electrode can be any useful conductive material. For example, the gate electrode may comprise doped silicon, or a metal, such as aluminum, chromium, copper, gold, silver, nickel, palladium, platinum, tantalum, and titanium. Conductive polymers also can be used, for example polyaniline, poly(3,4-ethylenedioxythiophene)/poly(styrene sulfonate) (PEDOT:PSS). In addition, alloys, combinations, and multilayers of these materials may be useful.

The gate dielectric is provided on the gate electrode, for example, through a deposition method. This gate dielectric electrically insulates the gate electrode under the operating conditions of the OTFT device from the balance of the device. Thus, the gate dielectric comprises an electrically insulating material. The gate dielectric should have a dielectric constant above about 2, more preferably above about 5. The dielectric constant of the gate dielectric also can be very high, for example, 80 to 100 or even higher. Useful materials for the gate dielectric may comprise, for example, an organic or inorganic electrically insulating material, or combinations thereof.

The gate dielectric may comprise a polymeric material, such as polyvinylidenefluoride (PVDF), cyanocelluloses, polyimides, epoxies, etc. In some embodiments, an inorganic capping layer comprises the outer layer of an otherwise polymeric gate dielectric for improved bonding to the polymeric layer and/or improved dielectric properties.

Specific examples of inorganic materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these can be used for the gate dielectric. Of these materials, aluminum oxides, silicon oxides, silicon nitrides, and zinc selenide are preferred.

The gate dielectric can be deposited in the OTFT as a separate layer, or formed on the gate such as by oxidizing, including anodizing, the gate material to form the gate dielectric.

The source electrode and drain electrode are separated from the gate electrode by the gate dielectric, while the organic semiconductor layer can be over or under the source electrode and drain electrode. The source and drain electrodes can be any useful conductive material. Useful materials include those materials described above for the gate electrode, for example, aluminum, barium, calcium, chromium, copper, gold, silver, nickel, palladium, platinum, titanium, polyaniline, PEDOT:PSS, other conducting polymers, alloys thereof, combinations thereof, and multilayers thereof.

The thin film electrodes (e.g., gate electrode, source electrode, and drain electrode) can be provided by any useful means such as physical vapor deposition (e.g., thermal evaporation, sputtering), plating, or ink jet printing. The patterning of these electrodes can be accomplished by known methods such as shadow masking, additive photolithography, subtractive photolithography, printing, transfer printing, microcontact printing, and pattern coating.

The organic semiconductor layer, produced in accordance with the present invention, can be provided by any useful means, such as for example, vapor deposition, solution deposition, spin coating, and printing techniques, all of which are well known in the art.

Importantly, the compounds of the present invention can be used in the manufacture of a wide range of electronic devices and semiconductor components, including but not limited to, Organic Thin Film Semiconductor (OTFS), an Organic Field-Effect Transistor (OFET), an Organic Light Emitting Diode (OLED), a solar cell, and a device for solar energy conversion.

EXAMPLES

Example 1

Synthesis of 1,4,5,8-Anthradiquinone

Two lengthy synthetic routes (>5 steps) to the desired 1,4,5,8-anthradiquinone (3) starting material have been reported, but large amounts of high purity material could not be obtained.[i] An alternative two-step preparation of anthradiquinone 3 was reported by Cory's group (Scheme 3);[ii] however, the yields for each reaction were below 50%. 1,4,5,8-Anthradiquinone (3) was a key intermediate in our route to pentacene, thus an optimized preparation of 3 was desired.

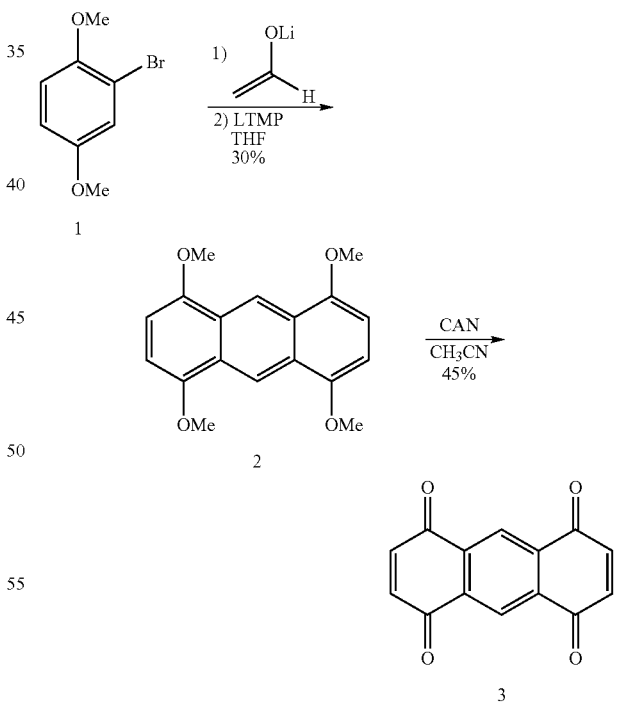

The first reaction that was attempted was the original procedure reported by Fitzgerald (Table 1, entry 1). A solution of lithium 2,2,6,6-tetramethylpiperidine (LTMP, 7) in THF was prepared by the addition of methyllithium to 2,2,6,6-tetramethylpiperidine (TMP). The LTMP solution was heated to reflux, bromide 1 was added, and heating was continued for one hour. The reaction was cooled to room temperature and poured into HCl (10% aq). A small amount (16% yield) of 1,4,5,8-tetramethoxyanthracene (2) was obtained. A violent evolution of gases occurred when bromide 1 was added to the boiling LTMP solution, preventing the reaction from being conducted on a larger scale. When bromide 1 was added to the LTMP solution at room temperature (23° C.) and then heated, little to no product was obtained.

TABLE 1

Reaction conditions for the preparation of 1,4,5,8-tetramethoxyanthracene (2).

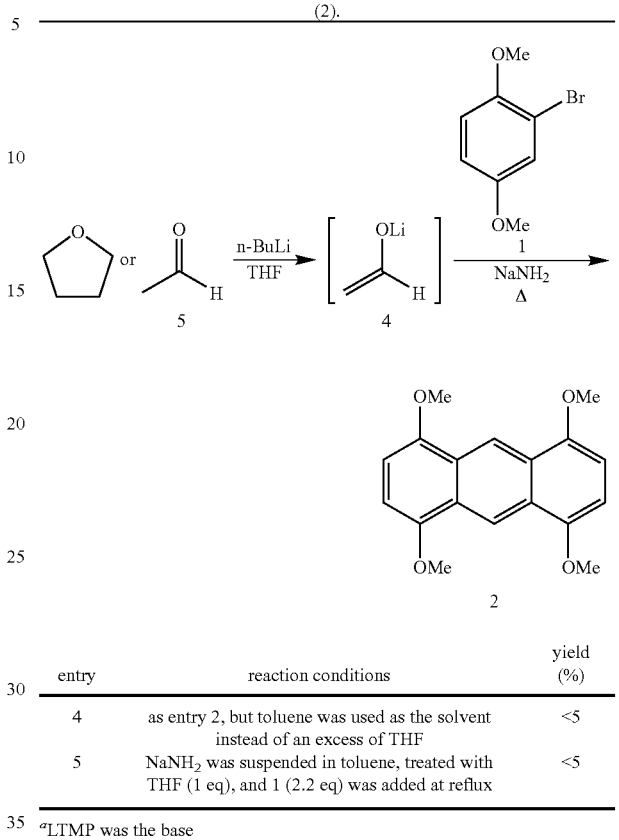

| entry | reaction conditions | yield (%) |
|---|---|---|
| 1[a] | TMP was treated with MeLi to form LTMP and 1 was added at reflux | 16 |
| 2 | enolate 4 was preformed from THF, transferred to a suspension of NaNH$_2$, and treated with 1 at reflux | 10-32 |
| 3 | enolate 4 was preformed from 5, transferred to a suspension of NaNH$_2$, and 1 was added at reflux | 28 |
| 4 | as entry 2, but toluene was used as the solvent instead of an excess of THF | <5 |
| 5 | NaNH$_2$ was suspended in toluene, treated with THF (1 eq), and 1 (2.2 eq) was added at reflux | <5 |

[a]LTMP was the base

The proposed mechanism for the transformation of bromide 1 to 1,4,5,8-tetramethoxyanthracene (2) is shown in Scheme.[iii] Benzyne 6 is formed from bromide 1 and is quenched with the lithium enolate of acetaldehyde (4) to give benzocyclobutane 8. Benzocyclobutane 8 could either be isolated (after protonation) or reacted in situ with a second equivalent of benzyne 6 to give 1,4,5,8-tetramethoxyanthracene (2) after dehydration and aromatization.

Scheme 4: Proposed mechanism for the preparation of 2 via a benzyne intermediate.[iii]

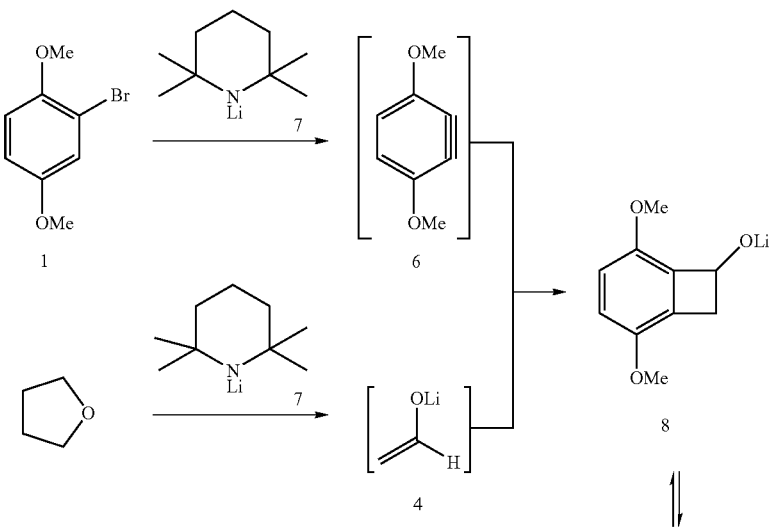

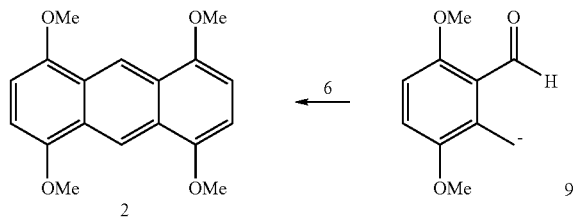

Cory's group obtained 1,4,5,8-tetramethoxyanthracene (2) in better yield (30%) when n-butyllithium was used to form enolate 4 from THF and sodium amide (NaNH$_2$) was used to generate benzyne 6 from bromide 1.[iv] When these reaction conditions were used with sodium amide pellets, no reaction occurred. A similar result was obtained with freshly powdered NaNH$_2$. When a suspension of NaNH$_2$ in toluene (commercially available from Aldrich) was used, varying amounts (10-32% yield) of 1,4,5,8-tetramethoxyanthracene (2) were obtained (Table, entry 2). Similar yields of 2 were obtained when acetaldehyde (5) was used as the enolate precursor instead of THF (entry 3).

In each of the procedures described above, THF was used as both a precursor for the lithium enolate of acetaldehyde (4) and as the reaction solvent. Lithium 2,2,6,6-tetramethylpiperidine (7) was shown to be a strong enough base to ring-open THF. If sodium amide has a similar reactivity toward THF, then an excess of enolate 4 would be formed and would react with benzyne 6 to give cyclobutane 8. This would result in a shortage of benzyne 6 for the reaction with anion 9 and lead to lower yields of 2.

The reaction solvent was changed from THF to toluene and stoichiometric amounts of THF and n-butyllithium were used to generate enolate 4 (Table 1, entry 4). Unfortunately, only a small amount of 2 (<5%) was obtained. The last optimization attempt involved using sodium amide to generate enolate 4 from THF and benzyne 6 from bromide 1. In this reaction sodium amide was suspended in toluene and THF (1 eq) was added to the reaction (entry 5). The reaction was heated to form enolate 4 and bromide 1 was added to the boiling reaction. Once again, only a small amount of 2 (<5%) was isolated. Despite numerous unsuccessful attempts at optimizing the synthesis of 1,4,5,8-tetramethoxyanthracene (2), we continued the synthesis using the material we could obtain using Cory's reaction conditions.

Oxidation of 2 to 1,4,5,8-anthradiquinone (3) using ceric ammonium nitrate (CAN) proceeded consistently in 40-60% yields, similar to the reported yield for the reaction. Optimization of this reaction is currently being explored by another Fallis group member.

Example 2

Synthesis of Silyl Ethers

With anthradiquinone 3 in hand we began studying the double Diels-Alder reaction and the inevitable separation of the resulting regioisomers. Danishefsky-type dienes readily undergo [4+2] cycloadditions with quinones and the reaction products are known to oxidize on silica gel in the presence of oxygen to the corresponding aromatic product (Scheme).[v]

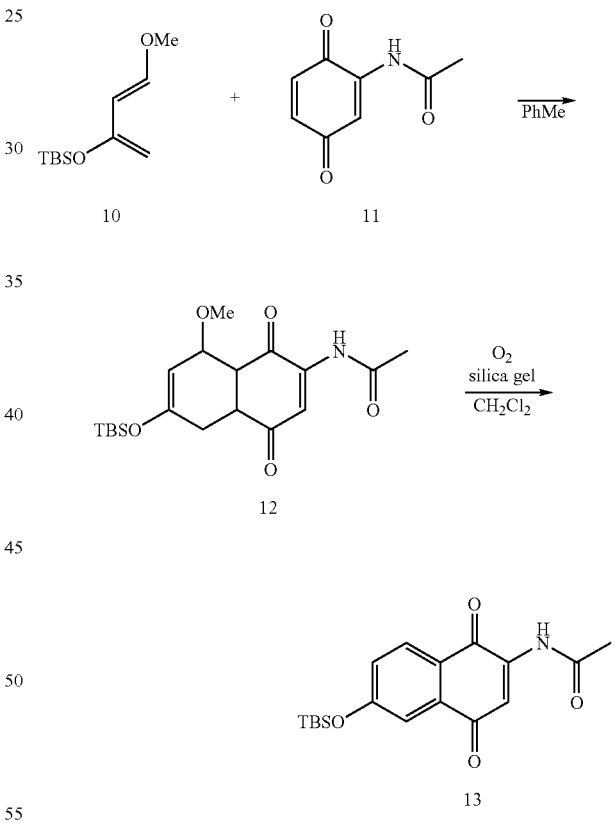

The first reaction that was conducted was a reaction of anthradiquinone 3 with Danishefsky's diene 14 (Scheme 6). After stirring the reaction overnight at room temperature all of anthradiquinone 3 was consumed, but the desired silyl ethers were not formed when the reaction was treated with silica gel. A proton NMR spectrum of the reaction product suggested that desilylation had occurred to give a mixture of 17 and 18 instead of elimination of methoxide and aromatization as desired.

Scheme 6: Double Diels-Alder reaction of anthradiquinone 3 and diene 14.

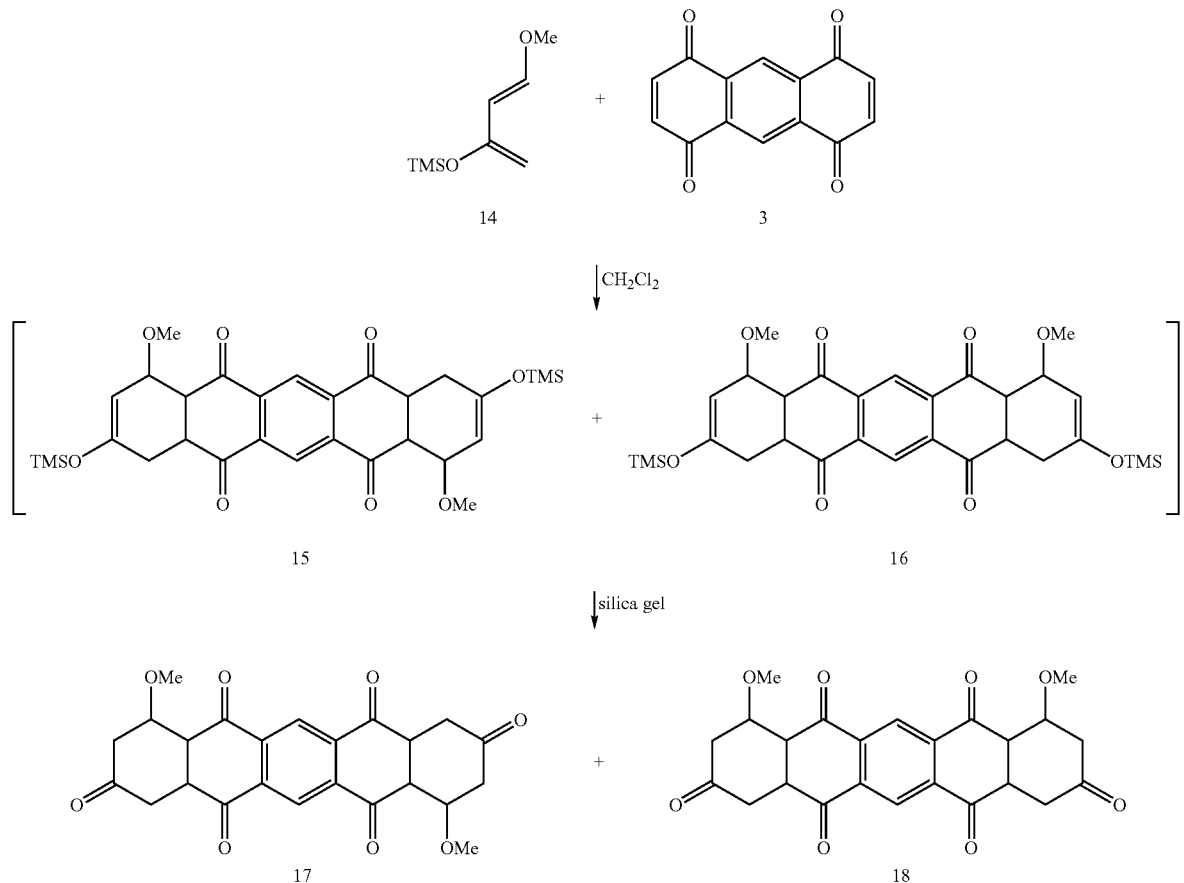

The double Diels-Alder reaction was repeated with a bulker t-butyldimethylsilyl Danishefsky's diene, 10, which was not as prone to hydrolysis as the trimethylsilyl ether (Scheme 7). Diene 10 and anthradiquinone 3 were combined in methylene chloride and stirred overnight at room temperature. Silica gel was added to the reaction and stirred open to air for 12 hours and two, less-polar spots were present on the TLC plate. The less polar compounds were isolated and determined to be silyl ethers 22 and 21, which were formed as a 1:1 mixture in varying 20-42% yields. The reaction yield was increased to 60% by changing the solvent from methylene chloride to THF prior to adding silica gel to the reaction. A simple filtration of the crude reaction mixture through a silica gel plug with methylene chloride gave silyl ethers 22 and 21. The overall transformation of diquinone 3 to the silyl ethers involved two cycloaddition reactions, elimination of two methoxy substituents, and aromatization of the two peripheral rings all in one pot.

Scheme 7: Double Diels-Alder reaction of diene 10 and anthradiquinone 3.

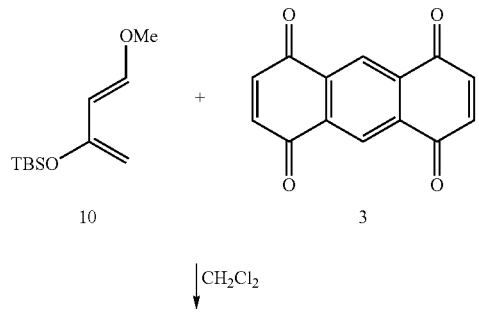

-continued

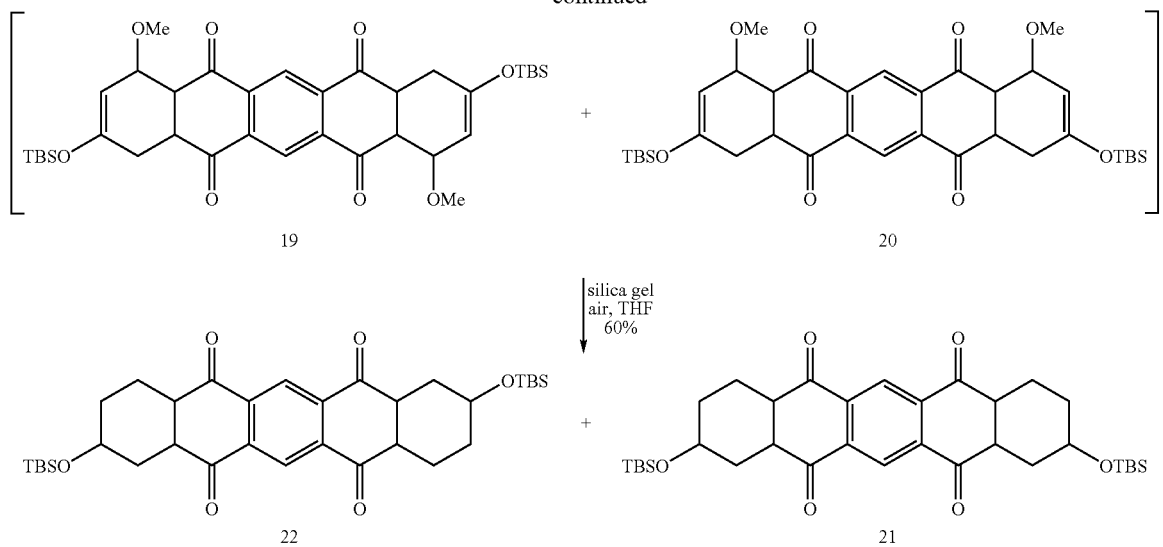

Separation of silyl ethers 22 and 21 proved to be difficult. Flash chromatography gave only one fraction of pure 22. Repeated chromatography did not afford a pure sample of 21, which was the second compound to elude. Preparative HPLC successfully separated the two isomers; however, the poor solubility of the silyl ethers in the mobile phase allowed only 25 mg of the mixture to be separated in a 45 minute run.

To separate the two isomers, a supersaturated solution of silyl ethers 22 and 21 was filtered and injected into the preparative HPLC. Over the course of ten injections, the ratio of 22 and 21 changed from 1:1 to 1:1.2, suggesting that silyl ether 22 was less soluble in the mobile phase than the other isomer. Encouraged by this finding, a fractional crystallization separation of the silyl ethers was attempted. The mixture of silyl ethers was heated in chloroform and cooled to 0° C. for 18 h. The crystals that were recovered were predominantly silyl ether 22. After three recrystallizations, analytically pure silyl ether 22 was obtained. Silyl ether 21 was enriched in the mother liquor. Although the purity of 21 was not as high (>90%), it was sufficiently pure to be used in future reactions as the minor impurity could be removed later in the synthesis.

The different symmetry of the two isomers allowed them to be identified by their $^1$H and $^{13}$C NMR spectra. Silyl ether 22 had $C_{2h}$ symmetry, was the less polar isomer (higher spot on TLC), and less soluble in chloroform than silyl ether 21. In contrast, silyl ether 21 had lower $C_{2v}$ symmetry.

A single crystal X-ray structure of silyl ether 22 was obtained by the slow evaporation of a chloroform solution and proved that the structural assignment of the two silyl ethers was correct. The pentacyclic core of the molecule is planar and forms sheets of edge-to-face π-stacked dimers.

Example 3

Preparation of Ditriflates

With the anticipated troublesome steps in our 2,9- and 2,10-disubstituted pentacene synthesis behind us, we turned our focus to the preparation of ditriflates 25 and 26. These key intermediates would allow a multitude of substituted pentacene derivatives to be prepared in order to study the effect of various functional groups on the electronics and solid-state packing of these compounds.

Treatment of a solution of silyl ether 22 in THF with TBAF at room temperature resulted in a deep blue solution that gave diol 24 as a pale yellow solid after the addition of water (Scheme). Diol 24 was recovered by filtration and was not soluble in organic solvents. In fact, diol 24 was only soluble in aqueous NaOH (10%), giving a deep blue solution. Diol 24 could not be characterized due to its poor solubility.

Scheme 8: Preparation of diol 24.

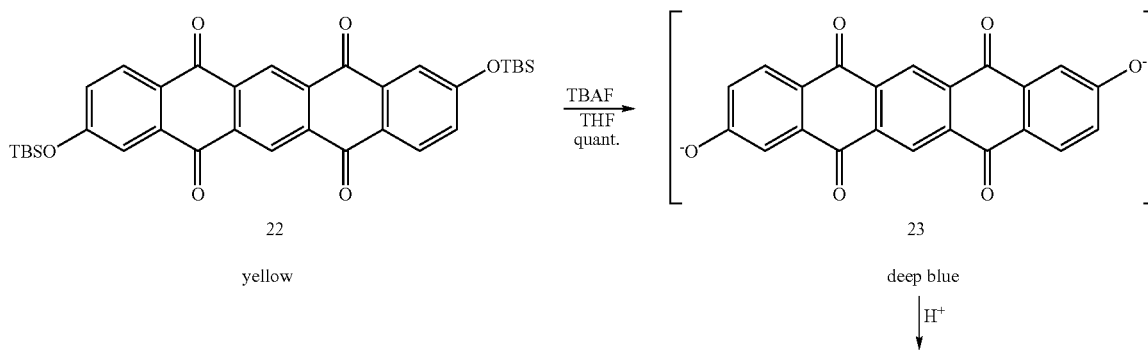

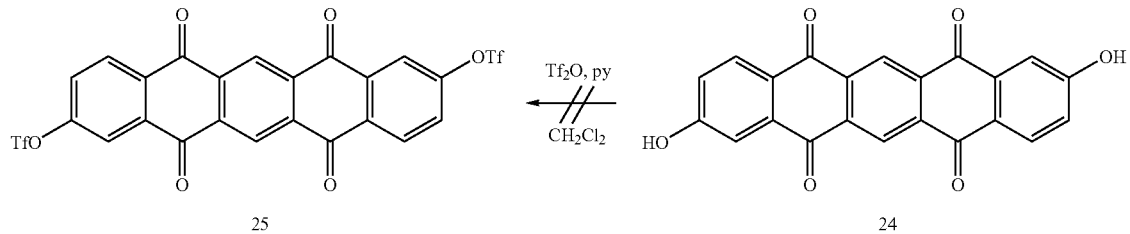

Numerous attempts to convert diol 24 to ditriflate 25 were unsuccessful (Table 2). When diol 24 was suspended in methylene chloride and treated with triflic anhydride (Tf$_2$O), both with and without a catalytic amount of DMAP, only the diol starting material was recovered (Table 2, entries 1 and 2). The reaction was attempted using pyridine as both the base and the reaction solvent with DMAP and triflic anhydride; however, starting material was recovered for reactions conducted at both room and elevated temperatures (entries 3 and 4). The same result was obtained when 2,6-lutidine was used in place of pyridine (entry 5). Numerous organic bases were surveyed in an attempt to solubilize diol 24 and generate the necessary anion, but in each case diol 24 did not react. This indicated that diol 24 was not in solution in any of these reactions.

TABLE 2

Attempted conversion of diol 24 to ditriflate 25.

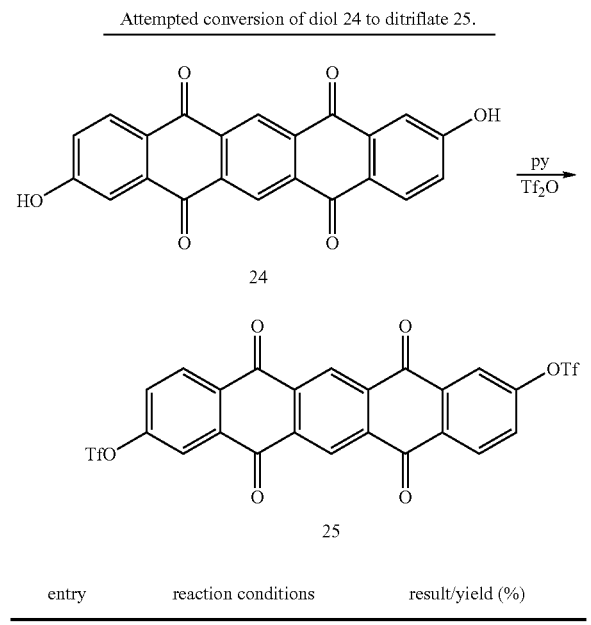

| entry | reaction conditions | result/yield (%) |
|---|---|---|
| 1 | CH$_2$Cl$_2$, 12 h, rt | recovered 24 |
| 2 | CH$_2$Cl$_2$, DMAP (cat.), 12 h, rt | recovered 24 |
| 3[a] | DMAP (cat.), 12 h, rt | recovered 24 |
| 4[a] | DMAP (cat.), 12 h, Δ | recovered 24 |
| 5[a,b] | DMAP (cat.), 12 h, rt | recovered 24 |
| 6[c] | TBAF, CH$_2$Cl$_2$, 12 h, rt | mixture of 25 and 24 |

TABLE 2-continued

Attempted conversion of diol 24 to ditriflate 25.

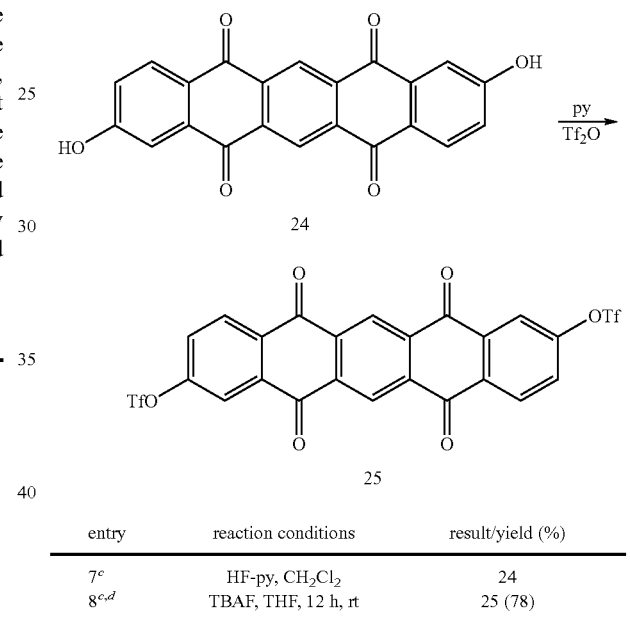

| entry | reaction conditions | result/yield (%) |
|---|---|---|
| 7[c] | HF-py, CH$_2$Cl$_2$ | 24 |
| 8[c,d] | TBAF, THF, 12 h, rt | 25 (78) |

[a]the base was used as the reaction solvent
[b]lutidine was used instead of pyridine
[c]silyl ether 22 was the substrate, not diol 24
[d]PhNTf$_2$ was used instead of Tf$_2$O A new strategy for forming ditriflate 25 was devised. The conversion of silyl ether 22 to diol 24 must pass through a dianion 23 intermediate. This same intermediate was required for the formation of ditriflate 25. Thus, silyl ether 22 was treated with two equivalents of TBAF to form the deep blue dianion, 23, which was then treated with triflic anhydride to give a mixture of diol 24, mono triflate, and ditriflate 25 (Table 2, entry 6). Encouraged by these results, the fluoride source was changed from TBAF[vi] to HF-pyridine, but only diol 24 was obtained. The best results were obtained when dianion 23 was formed from silyl ether 22 using TBAF in THF followed by treatment with N,N-bis(trifluoromethylsulfonyl)aniline,[vii] which is a triflating reagent that is compatible with THF (Table 2, entry 8 and Scheme 9). Ditriflate 25 was only sparingly soluble in THF and virtually insoluble in all other organic solvents.

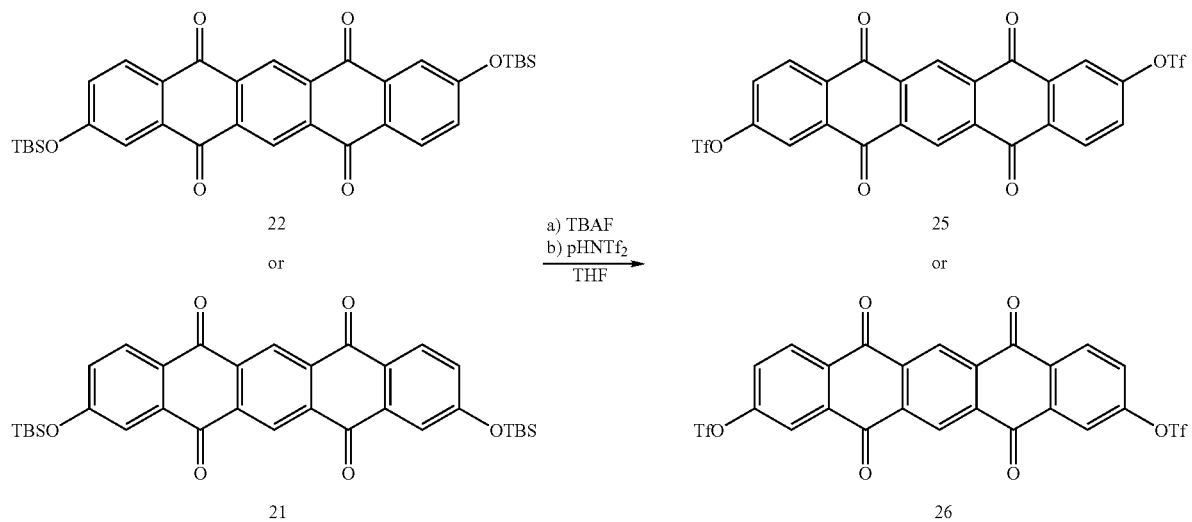

Scheme 9: Desilylation/triflation of silyl ethers 22 and 21 to afford ditriflates 25 and 26.

One puzzling observation was that either diol 24 or monotriflate was present in the crude product mixture, regardless of the amount of TBAF or triflating reagent that was used. Workup of the one-pot desilylation/triflation reaction involved suspending the reaction in a mixture of THF/ether and successively washing with HCl (10% aq), NaOH (10% aq) and water. The organic phase was concentrated to give ditriflate 25 in varying yields. During the NaOH wash the aqueous phase turned blue, which was indicative of anion formation.

The varying yields obtained in desilylation/triflation reaction prompted an examination of the workup. One concern was that the hydroxide ion was nucleophilic enough to react with ditriflate 25, either by attacking one of the quinone carbonyls or the triflate. When the reaction was worked up with a NaHCO$_3$ (sat. aq) wash instead of the NaOH (10% aq) wash, ditriflate 25 was isolated in greater than 90% yield. When an authentic sample of ditriflate 25 was suspended in THF/ether and treated with NaOH (10% aq), a blue solution characteristic of dianion 23 formed. Treatment of this solution with acid afforded diol 24. This provided conclusive evidence that the hydroxide ion was reacting with ditriflate 25.

Ditriflates 25 and 26 could both be made by the desilylation/triflation procedure to give crude material in nearly quantitative yield. This product was used without further purification in the palladium coupling reactions described in the next section.

Example 4

Preparation of 2,9- and 2,10-Disubstituted Pentacenes

The rapid route to ditriflates 25 and 26 was a major milestone in the synthesis of 2,9- and 2,10-disubstituted pentacenes, as an assortment of functionalized pentacene compounds could be accessed from ditriflates 25 and 26 via palladium coupling reactions. Pentacenes 29 and 31 possessing triisopropylsilylethynyl substituents in the 2,9 or 2,10 positions were the first targets. Anthony's group predicted pentacene 29 would be well-organized in the solid-state, allowing for significant intermolecular orbital overlap, and in turn, possess higher electron and hole mobilities.

A Sonogashira reaction of ditriflate 25[viii] and TIPS-acetylene in the presence of Pd(PPh$_3$)$_2$Cl$_2$, CuI, and Et$_3$N in THF gave diquinone 27 (Scheme 10). Ditriflate 25 was sparingly soluble in THF (1 mg/5 mL) and decent yields (76%) of diquinone 27 were obtained only when 25 was completely dissolved prior to the addition of the other reagents. The use of DMF as a cosolvent did not improve the solubility of 25 or the reaction yield. Diquinones 27 and 28 were readily soluble in THF and chlorinated solvents and could be purified by recrystallization from ether.

Scheme 10: Preparation of diquinones 27 and 28.

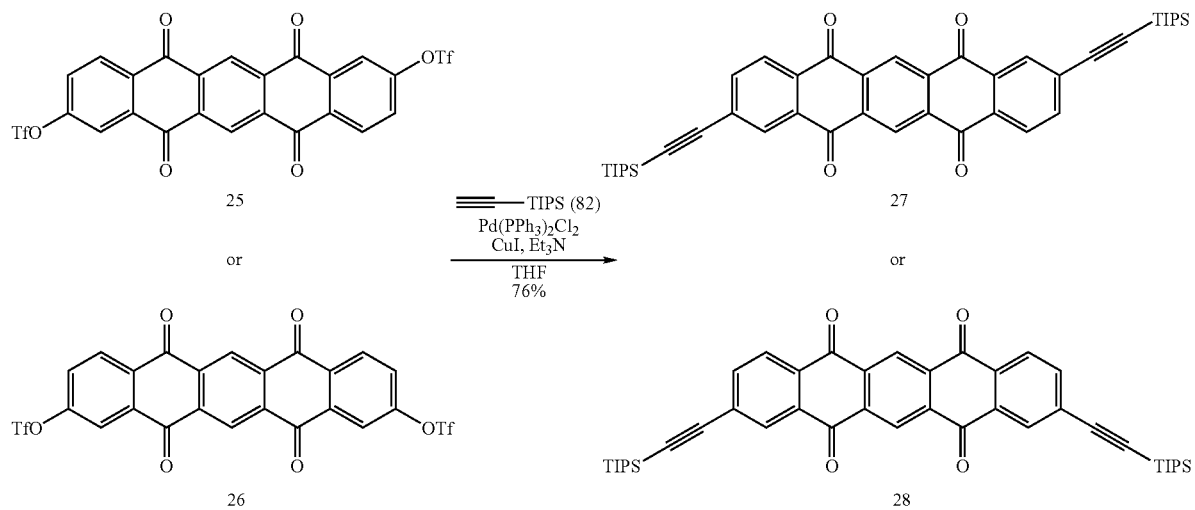

A number of procedures are known for the reduction of anthraquinones (and related compounds) to their corresponding deoxygenated, aromatic species. The most common procedures are zinc powder and catalytic copper(II) sulphate in ammonium hydroxide[ix] or aluminum amalgam ammonium hydroxide.[x] When these reaction conditions were used to reduce diquinone 27, a complex mixture was obtained (Table 3, entries 1 and 2). However, when diquinone 27 was treated with a large excess of sodium borohydride in refluxing isopropanol,[xi] pentacene 29 was isolated in an excellent yield (88%) (Table 3, entry 3). Reaction workup and product purification remains to be optimized.

TABLE 3

Reaction conditions for the reduction of diquinone 27 to pentacene 29.

| entry | reaction conditions | result (%) |
| --- | --- | --- |
| 1 | Zn(s), Cu(II)SO$_4$ (cat.), NH$_4$OH, Δ | mixture |
| 2 | Al/Hg, NH$_4$OH, Δ | mixture |
| 3 | NaBH$_4$, i-PrOH, Δ | 29 (88) |

During the preparation of an NMR sample of pentacene 29, the initial purple solution rapidly turned bright yellow. The resulting $^1$H NMR spectrum contained a peak at δ4.19, which is characteristic of a methyne, bridgehead proton. There are numerous reports of acenes reacting with oxygen to give endoperoxides.[xii] With this in mind, we suspected that pentacene 29 acted as its own photooxygenation sensitizer leading to the formation of endoperoxide 30 (Scheme 11).[xiii] To test this hypothesis, a solution of pentacene 29 was prepared in an inert atmosphere (glovebox) and the methylene chloride solution remained purple.

Scheme 11: Reaction of pentacene 29 with O$_2$ to give endoperoxide 30.

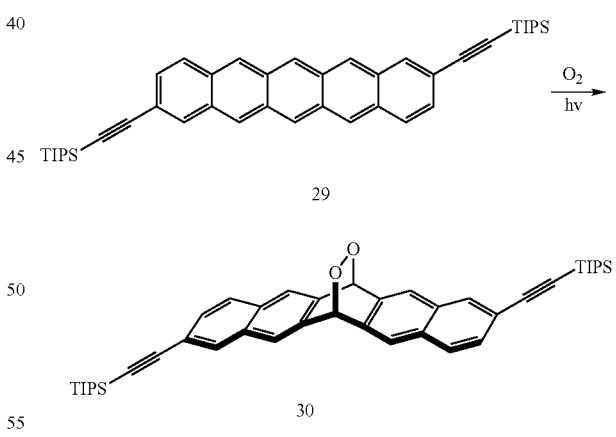

While the invention has been described with reference to particular preferred embodiments thereof, it will be apparent to those skilled in the art upon a reading and understanding of the foregoing that numerous methods for substituted pentacene production, other than the specific embodiments illustrated are attainable, which nonetheless lie within the spirit and scope of the present invention. It is intended to include all such designs, assemblies, assembly methods, and equivalents thereof within the scope of the appended claims. With particular reference to the synthetic methods of the present invention, each method as claimed is intended to encompass obvious chemical equivalents thereof.

REFERENCES i. (a) Boldt, P.; Vardakis, F. *Angew. Chem., Int. Ed. Engl.* 1965, 4, 1078; (b) Almlof, J. E.; Feyereisen, M. W.; Jozefiak, T. H.; Miller, L. L. *J. Am. Chem. Soc.* 1990, 112, 1206.
ii. Cory, R. M.; McPhail, C. L.; Dikmans, A. J. *Tetrahedron Lett.* 1993, 34, 7533.
iii. (a) Fitzgerald, J. J.; Drysdale, N. E.; Olofson, R. A. *Synth. Commun.* 1992, 22, 1807; (b) Fitzgerald, J. J.; Drysdale, N. E.; Olofson, R. A. *J. Org. Chem.* 1992, 57, 7122.
iv. Cory, R. M. Personal Correspondence—Apr. 11, 2002 (e-mail).
v. (a) Danishefsky, S. J.; Kitahara, T.; Yan, C. F.; Morris, J. *J. Am. Chem. Soc.* 1979, 101, 6996; (b) Danishefsky, S. J.; Yan, C. F.; Singh, R. K.; Gammill, R. B.; McCurry, P.; Fritsch, N.; Clardy, J. C. *J. Am. Chem. Soc.* 1979, 101, 7001.
vi. X-ray data for silyl ether 247.
vii. TBAF was used as a solution in THF. $Tf_2O$ reacts with THF and reduces the effective amount of $Tf_2O$ in the reaction. Better yields were obtained when excess $Tf_2O$ was used.
viii. Hendrickson, J. B.; Bergeron, R. *Tetrahedron Lett.* 1973, 14, 4747.
ix. A review on the synthesis of aryl and vinyl triflates and their reactions including palladium couplings: Ritter, K. *Synthesis* 1993, 735.
x. Rewcastle, G. W.; Atwell, G. J.; Palmer, B. D.; Boyd, P. D. W.; Baguley, B. C.; Denny, W. A. *J. Med. Chem.* 1991, 34, 491.
xi. (a) Petti, M. A.; Shepodd, T. J.; Barrans Jr., R. E.; Dougherty, D. A. *J. Am. Chem. Soc.* 1988, 110, 6825; (b) Goodall, F. L.; Perkin, A. G. *J. Chem. Soc.* 1923, 470; (c) Hall, J.; Perkin, A. G. *J. Chem. Soc.* 1923, 2029.
xii. Tius, M. A.; Gomez-Galeno, J.; Zaidi, J. H. *Tetrahedron Lett.* 1988, 29, 6909.
xiii. Aubry, J.-M.; Pierlot, C.; Rigaudy, J.; Schmidt, R. *Acc. Chem. Res.* 2003, 36, 668.
xiv. A crystal structure of a related endoperoxide was recently published: Schuster, I. I.; Craciun, L.; Ho, D. M.; Pascal, R. A. Jr. *Tetrahedron* 2002, 58, 8875.

The invention claimed is:

1. A method for the preparation of a compound comprising at least one linear series of five fused carbon rings, the method comprising the steps of:
   (a) providing an unsubstituted or substituted 1,4,5,8-anthradiquinone of the general formula I:

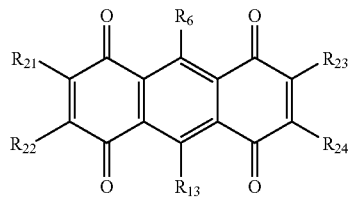

(I)

wherein each R group is independently selected from the group consisting of hydrogen, an electron-withdrawing group, halogen, trialkylsilylalkynyl, and amine;
   (b) providing an unsubstituted or substituted acyclic, cyclic, or heterocyclic diene of the general formula IIa or IIb:

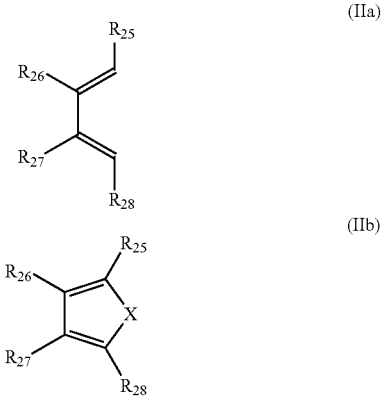

wherein each R group is independently selected from the group consisting of hydrogen, an electron-withdrawing group, halogen, trialkylsilyl trialkylsilylalkynyl, alkoxy, aryloxy, and amine, and X is C, O, S, or N;
   (c) performing a double or stepwise cycloaddition reaction between the 1,4,5,8-anthradiquinone and the diene to generate a core structure comprising five fused carbon rings sequentially identified as rings A, B, C, D, and E in the compound of formula III:

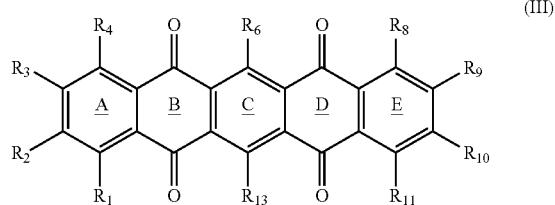

wherein each R group is as previously defined.

2. The method of claim 1, further comprising the steps of:
   (d) performing a ring opening reaction to convert a bridged form of each of rings A and E to an unbridged form; and
   (e) optionally performing an aromatization reaction or equivalent on the A, and E rings of the core structure;
   wherein steps (d) and (e) can be performed in any order.

3. The method of claim 1, wherein isomeric products are generated, the method further comprising the step of:
   (d) replacing or adding selected substituents.

4. The method of claim 1, further comprising the step of:
   (d) subjecting the compound to reducing conditions to generate a corresponding unsubstituted or substituted pentacene.

5. The method of claim 1, further comprising the step of:
   (d) separating isomeric products.

6. The method of claim 1, further comprising the step of:
   (d) performing a coupling reaction to link two or more core structures.

7. The method of claim 1, wherein step (c) comprises a double Diels-Alder reaction between the anthradiquinone and two diene molecules.

8. The method of claim 1, wherein in step (b) $R_{26}$ or $R_{27}$ comprises A-B, wherein A is a protective group, and B is a group to be protected, and wherein the method generates an compound of the formula III:

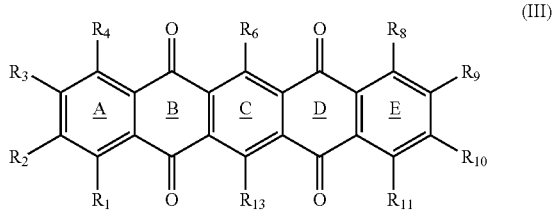

(III)

wherein $R_2$, and $R_9$ or $R_{10}$ are A-B, and each remaining R is each independently unsubstituted or substituted.

9. The method of claim 8, wherein further comprising replacing each A-B at $R_2$, and $R_9$ or $R_{10}$ with an alternative substituent.

10. The method of claim 4, wherein the step of reducing generates a pentacene compound of formula IV:

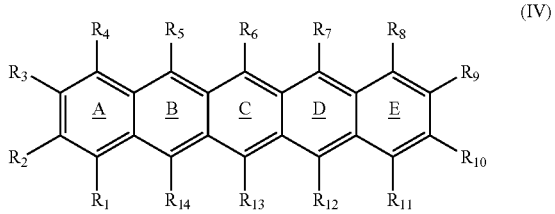

(IV)

wherein $R_2$, and $R_9$ or $R_{10}$ are A-B, and each remaining R is each independently unsubstituted or substituted.

11. The method of claim 10, further comprising replacing each A-B at $R_2$, and $R_9$ or $R_{10}$ with an alternative substituent.

12. The method of claim 11, wherein $R_2$, and $R_9$ or $R_{10}$ comprise an unsubstituted or substituted group selected from acetylene, alkyl, aryl, heteroaryl, alkenyl, and alkynyl.

13. The method of claim 12, wherein $R_2$ and $R_9$ or $R_{10}$ comprise acetylene or a linker comprising one or more triple bonds, optionally substituted by halogen and/or triflate.

14. The method of claim 6, wherein the method comprises step (d) thereby to generate an oligomeric compound comprising multiple units of said core structure linked by acetylene groups at the 2, and 9 or 10 positions.

15. The method of claim 10, wherein each A-B comprises $Si(R_{30}, R_{31}, R_{32})$ wherein each of $R_{30}$, $R_{31}$, $R_{32}$ in conjunction with Si acts to provide a protective group.

16. The method of claim 15, wherein each A-B comprises TMS, TES, TBS, TIPS, diphenyl tertiary butyl, OSi, OH, OTf, OTs, OMs, ONs, NSi, acetylene, phthalocyanine as a metal complex or free ligand, fullerene, Buckminsterfullerene $C_{60}R_{100}$, wherein $R_{100}$ is hydrogen or any substituent, or fullerene linked to the pentacene core via acetylene, or Buckminsterfullerene $C_{60}R_{100}$ linked to the pentacene core via acetylene, or phthalocyanine as a metal complex or free ligand linked to the pentacene core via acetylene.

17. The method of claim 16, wherein each B is O, S, Se, or N.

18. The method of claim 3, wherein in the step of replacing or adding selected substituents comprises replacing each A-B with Tf-O, halogen, or a substituent comprising a metal atom selected from Al, B, Cu, Co, Cr, Fe, Li, Mg, Ni, Pd, Pt, Si, Sn, Ti, and Zn.

19. The method of claim 18, wherein the method further comprises replacing each Tf-O with an acetylene group, or a group comprising a linker comprising one or more triple bonds.

20. The method of claim 5, wherein the step of separating comprises high performance liquid chromatography or fractional crystallization.

21. The method of claim 1, wherein $R_{25}$ is a leaving group comprising OAlk, NAlk, or halide, wherein each Alk comprises an alkyl group of from 1 to 12 carbon atoms.

22. The method of claim 1 for the preparation of a pentacene comprising substitutions at least at the 2 positions, and the 9 or 10 position, the method comprising the steps of:

(a) performing a stepwise or double Diels-Alder reaction by reacting a compound of formula IIa or IIb:

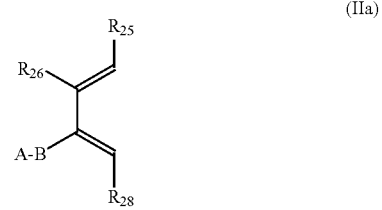

(IIa)

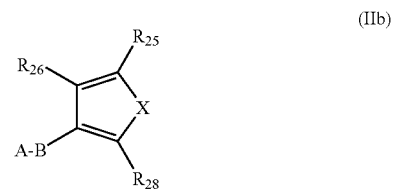

(IIb)

wherein A is a protective group, B is a group to be protected, and each R group is independent selected from H or a substituent, and X is C, O, S, or N, with a compound of formula I:

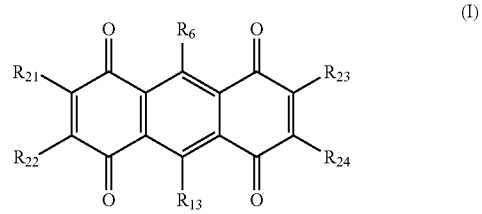

(I)

wherein each R group is independently selected from H or a substituent, and if necessary (b) optionally performing a ring opening reaction to covert a bridged form of each of rings A and E, to an unbridged form; and (c) optionally performing an aromatization reaction or equivalent on the A, and E rings of the core structure;

wherein the method generates a mixture of compounds of formula V and VI:

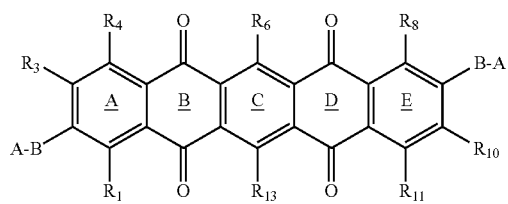
(V)

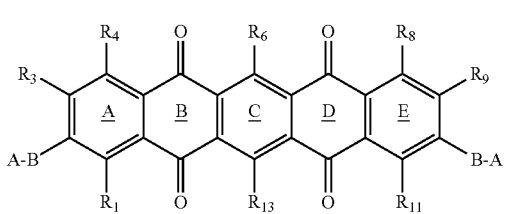
(VI)

wherein A is a protective group, B is a group to be protected, and each R group is independent selected from H or a substituent.

23. The method of claim 22 further comprising the step of:
   (c) separating the compounds of formula (V) and formula (VI), and selecting the compound of formula (V) and/or the compound of formula (VI) for further processing.

24. The method of claim 22 further comprising the step of:
   (c) replacing each A or each A-B with an alternative substituent, with or without a linker comprising one or more triple bonds to form a 2,9- and/or a 2,10-disubstituted diquinone.

25. The method of claim 22 further comprising the step of:
   (c) subjecting the 2,9- and/or the 2,10-disubstituted diquinone to reducing conditions to generate a pentacene substituted at least in the 2 position, and the 9 or 10 position.

\* \* \* \* \*